US011413035B2

(12) United States Patent
Korman et al.

(10) Patent No.: US 11,413,035 B2
(45) Date of Patent: Aug. 16, 2022

(54) SOFT TISSUE REPAIR INSTRUMENTS AND TECHNIQUES

(71) Applicant: Wright Medical Technology, Inc., Memphis, TN (US)

(72) Inventors: Zachary Korman, Memphis, TN (US); Lewis Pearce Branthover, Memphis, TN (US)

(73) Assignee: WRIGHT MEDICAL TECHNOLOGY, INC., Memphis, TN (US)

(*) Notice: Subject to any disclaimer, the term of this patent is extended or adjusted under 35 U.S.C. 154(b) by 347 days.

(21) Appl. No.: 16/495,136

(22) PCT Filed: Jun. 30, 2017

(86) PCT No.: PCT/US2017/040278
§ 371 (c)(1),
(2) Date: Sep. 18, 2019

(87) PCT Pub. No.: WO2019/005102
PCT Pub. Date: Jan. 3, 2019

(65) Prior Publication Data
US 2021/0186487 A1 Jun. 24, 2021

(51) Int. Cl.
*A61B 17/04* (2006.01)
*A61B 17/06* (2006.01)
*A61B 17/062* (2006.01)

(52) U.S. Cl.
CPC ...... *A61B 17/0482* (2013.01); *A61B 17/0469* (2013.01); *A61B 17/0485* (2013.01);
(Continued)

(58) Field of Classification Search
CPC ............ A61B 17/0482; A61B 17/0469; A61B 17/0485; A61B 17/06066; A61B 17/062;
(Continued)

(56) References Cited

U.S. PATENT DOCUMENTS

| 3,638,653 A | 2/1972 | Berry |
| 3,638,654 A | 2/1972 | Akuba |

(Continued)

FOREIGN PATENT DOCUMENTS

| JP | 20144144232 A | 8/2014 |
| WO | WO2012068002 A1 | 5/2012 |
| WO | 2016148904 A1 | 9/2016 |

OTHER PUBLICATIONS

International Search Report and Written Opinion issued in connection with corresponding International Patent Application No. PCT/US2017/040278, dated Feb. 26, 2018, 17 pages.

(Continued)

*Primary Examiner* — George J Ulsh
(74) *Attorney, Agent, or Firm* — Duane Morris LLP

(57) ABSTRACT

A method includes passing a first flexible strand through a tissue section by a first needle coupled to a driver. The driver includes a longitudinal body defining an opening at a distal end. The first needle is positioned in the opening. A first hole is formed through a bone. The first flexible strand is passed through the first hole using a strand retriever. The strand retriever includes a body having a first longitudinal tube extending therefrom and a first snare slideably deployable from the first longitudinal tube. The first longitudinal tube is positioned from a first side of the bone in the first hole and the first snare is deployed on a second side of the bone. The first snare passes the first flexible strand through the first hole in the bone. The tissue section is secured to the bone using the first flexible strand.

9 Claims, 41 Drawing Sheets

(52) U.S. Cl.
CPC ...... *A61B 17/062* (2013.01); *A61B 17/06066* (2013.01); *A61B 2017/0474* (2013.01); *A61B 2017/06076* (2013.01)

(58) Field of Classification Search
CPC .. A61B 2017/0474; A61B 2017/06076; A61B 17/1775; A61B 17/8866
See application file for complete search history.

(56) References Cited

U.S. PATENT DOCUMENTS

| | | | |
|---|---|---|---|
| 4,034,763 A | 7/1977 | Frazier | |
| 4,527,564 A | 7/1985 | Yasukata et al. | |
| 5,041,127 A | 8/1991 | Troutman | |
| 5,356,424 A | 10/1994 | Buzerak et al. | |
| 5,499,991 A | 3/1996 | Garman et al. | |
| 5,935,138 A | 8/1999 | McJames, II et al. | |
| 5,984,933 A | 11/1999 | Yoon | |
| 5,988,171 A | 11/1999 | Sohn et al. | |
| 6,022,360 A | 2/2000 | Reimels et al. | |
| 6,224,611 B1 | 5/2001 | Ouchi | |
| 6,315,784 B1 | 11/2001 | Djurovic | |
| 6,355,050 B1 | 3/2002 | Andreas et al. | |
| 7,967,832 B2 * | 6/2011 | Chu | A61B 17/0482 606/144 |
| 8,202,282 B2 | 6/2012 | Schmieding et al. | |
| 8,888,849 B2 | 11/2014 | Fallin et al. | |
| 9,271,724 B2 | 3/2016 | Arnett et al. | |
| 9,326,791 B2 | 5/2016 | Yeung et al. | |
| 9,339,267 B2 * | 5/2016 | Dreyfuss | A61B 17/0057 |
| 9,351,721 B2 | 5/2016 | Auerbach et al. | |
| 9,357,997 B2 * | 6/2016 | Sinnott | A61B 17/0491 |
| 10,278,690 B2 * | 5/2019 | Skinlo | A61B 17/0469 |
| 10,383,620 B2 * | 8/2019 | Harrison | A61B 17/0482 |
| 2001/0002436 A1 | 5/2001 | Bowman et al. | |
| 2001/0023352 A1 | 9/2001 | Gordon et al. | |
| 2003/0233106 A1 | 12/2003 | Dreyfuss | |
| 2007/0118151 A1 * | 5/2007 | Davidson | A61B 17/0469 606/151 |
| 2007/0149986 A1 | 6/2007 | Morris et al. | |
| 2008/0027468 A1 | 1/2008 | Fenton et al. | |
| 2008/0312689 A1 | 12/2008 | Diduch et al | |
| 2009/0018554 A1 | 1/2009 | Thorne et al. | |
| 2009/0082788 A1 | 3/2009 | Elmaraghy | |
| 2010/0168505 A1 | 7/2010 | Inman et al. | |
| 2010/0198235 A1 | 8/2010 | Pierce et al. | |
| 2010/0249809 A1 | 9/2010 | Singhatat et al. | |
| 2010/0305581 A1 | 12/2010 | Hart | |
| 2011/0071550 A1 | 3/2011 | Diduchi et al. | |
| 2011/0077670 A1 | 3/2011 | Modesitt et al. | |
| 2011/0118757 A1 | 5/2011 | Pierce | |
| 2011/0295279 A1 | 12/2011 | Stone et al. | |
| 2012/0071901 A1 | 3/2012 | Heneveld | |
| 2012/0283753 A1 | 11/2012 | Saliman et al. | |
| 2013/0023906 A1 | 1/2013 | Kubalak | |
| 2013/0165954 A1 | 6/2013 | Dreyfuss et al. | |
| 2013/0184818 A1 | 7/2013 | Coughlin et al. | |
| 2013/0190782 A1 | 7/2013 | Nason | |
| 2013/0245644 A1 | 9/2013 | Tegels | |
| 2013/0245647 A1 | 9/2013 | Martin et al. | |
| 2013/0282029 A1 | 10/2013 | Skinlo et al. | |
| 2014/0188138 A1 | 7/2014 | Melsheimer et al. | |
| 2014/0194906 A1 | 7/2014 | Topper et al. | |
| 2014/0207158 A1 | 7/2014 | Stone et al. | |
| 2014/0228865 A1 | 8/2014 | Weisel et al. | |
| 2014/0257377 A1 | 9/2014 | Shinichi | |
| 2014/0277457 A1 | 9/2014 | Yeung et al. | |
| 2014/0316442 A1 | 10/2014 | Loenen et al. | |
| 2015/0025550 A1 | 1/2015 | Heneveld | |
| 2015/0038995 A1 | 2/2015 | Malkowski | |
| 2015/0073441 A1 * | 3/2015 | Fallin | A61B 17/0482 606/144 |
| 2015/0073477 A1 * | 3/2015 | Holmes, Jr. | A61B 17/842 606/232 |
| 2015/0088167 A1 | 3/2015 | Chin et al. | |
| 2015/0133946 A1 | 5/2015 | Horvath et al. | |
| 2015/0282806 A1 | 10/2015 | Jorgensen et al. | |
| 2016/0089150 A1 | 3/2016 | Hammerland, III et al. | |
| 2016/0174966 A1 | 6/2016 | Djurovic | |
| 2016/0183934 A1 | 6/2016 | Sanders et al. | |
| 2016/0220238 A1 | 8/2016 | Heneveld | |
| 2016/0338692 A1 | 11/2016 | Darois et al. | |

OTHER PUBLICATIONS

First Office Action issued in connection with Canadian Patent Application No. 3,057,602, dated Nov. 27, 2020, 6 pages.
First Examination Report issued in connection with Australian Patent Application No. 2017420762, dated Mar. 31, 2020, 4 pages.
Extended European Search Report issued in connection with corresponding European Patent Application No. 17916168.2, 15 pages, dated Mar. 9, 2021.
First Examination Report issued in connection with corresponding Australian Patent Application No. 2020270509, 7 pages, dated Apr. 13, 2022.

* cited by examiner

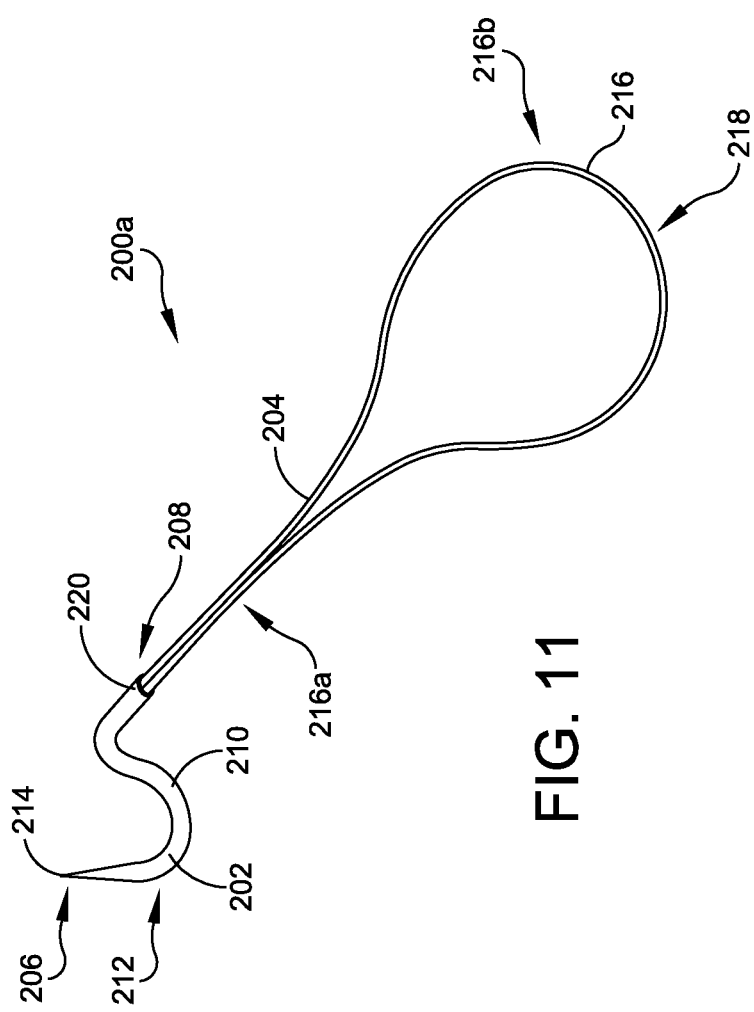

SOFT TISSUE REPAIR INSTRUMENTS AND TECHNIQUES

CROSS REFERENCE TO RELATED APPLICATION

This is a National Stage Application, filed under 35 U.S.C. 371, of International Patent Application No. PCT/US2017/040278, filed on Jun. 30, 2017, contents of which is incorporated herein by reference in its entirety.

BACKGROUND

Lesser metatarsophalangeal (MTP) joint instability can occur due to a tear in the plantar plate of the MTP joint. The plantar plate originates on the metatarsal head just proximal to the metatarsal articular surface and inserts onto the plantar base of the proximal phalanx. The plantar plate stabilizes and cushions the MTP joint during weight bearing. Early stages of MTP joint instability can present as pain or subtle deviation of the toes. Late stages can present as one toe crossing over another.

Although non-operative treatment measures can be used to reduce pain, such treatments rarely alter the progression of symptoms or malalignment. Non-steroidal anti-inflammatory drugs (NSAIDS) may be used to manage discomfort but do not correct the underlying symptoms or malalignment. Selective corticosteroid injections may be considered but they can potentially mask symptoms allowing for future worsening of the pathology. Non-operative treatment measures may temporarily relieve symptoms but will not permanently correct the deformity.

SUMMARY

In various embodiments, a method is disclosed. The method includes passing a first flexible strand through a first tissue section. The first flexible strand is passed through the first tissue by a first needle coupled to a driver. The driver comprising a longitudinal body defining an opening at a distal end. The first needle is positioned in the opening. A first hole is formed through a first bone adjacent to the first tissue section. The first suture is passed through the first hole using a strand retriever. The strand retriever comprises a body having a first longitudinal tube extending therefrom and a first snare slideably deployable from the first longitudinal tube. The first longitudinal tube is positioned from a dorsal side of the bone within the first hole formed in the first bone and the first snare is deployed on a plantar side of the bone. The first snare passes the first flexible strand through the first hole in the first bone. The first tissue section is secured to the first bone using the first flexible strand.

In various embodiments, a device is disclosed. The device includes a body extending along a longitudinal axis from a first end to a second end. The body defines a cavity extending from the first end to the second end and a needle opening extending through the second end to the cavity. The needle opening has a non-circular cross-section. A needle includes a non-circular mating end sized and configured to insertion into the needle opening of the body. The non-circular cross-section of the needle opening and the non-circular mating end of the needle maintain the needle in a fixed position with respect to the body and transfer a torsional force from the body to the needle.

In various embodiments, a kit is disclosed. The kit includes a strand retriever. The strand retriever includes a body defining an inner cavity. A first longitudinal tube and a second longitudinal tube each extend from a first side of the body. A first snare and a second snare are each slideably deployable from a first position in which each of the first snare and the second snare are substantially positioned within respective first and second longitudinal tubes and each have a distal end extending therefrom to a second position in which the first snare and the second snare are substantially positioned distally of respective first and second longitudinal tubes.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein:

FIG. 11 illustrates an isometric view of a needle construct including a corkscrew needle coupled to a flexible strand, in accordance with some embodiments.

DETAILED DESCRIPTION

Figure 1:
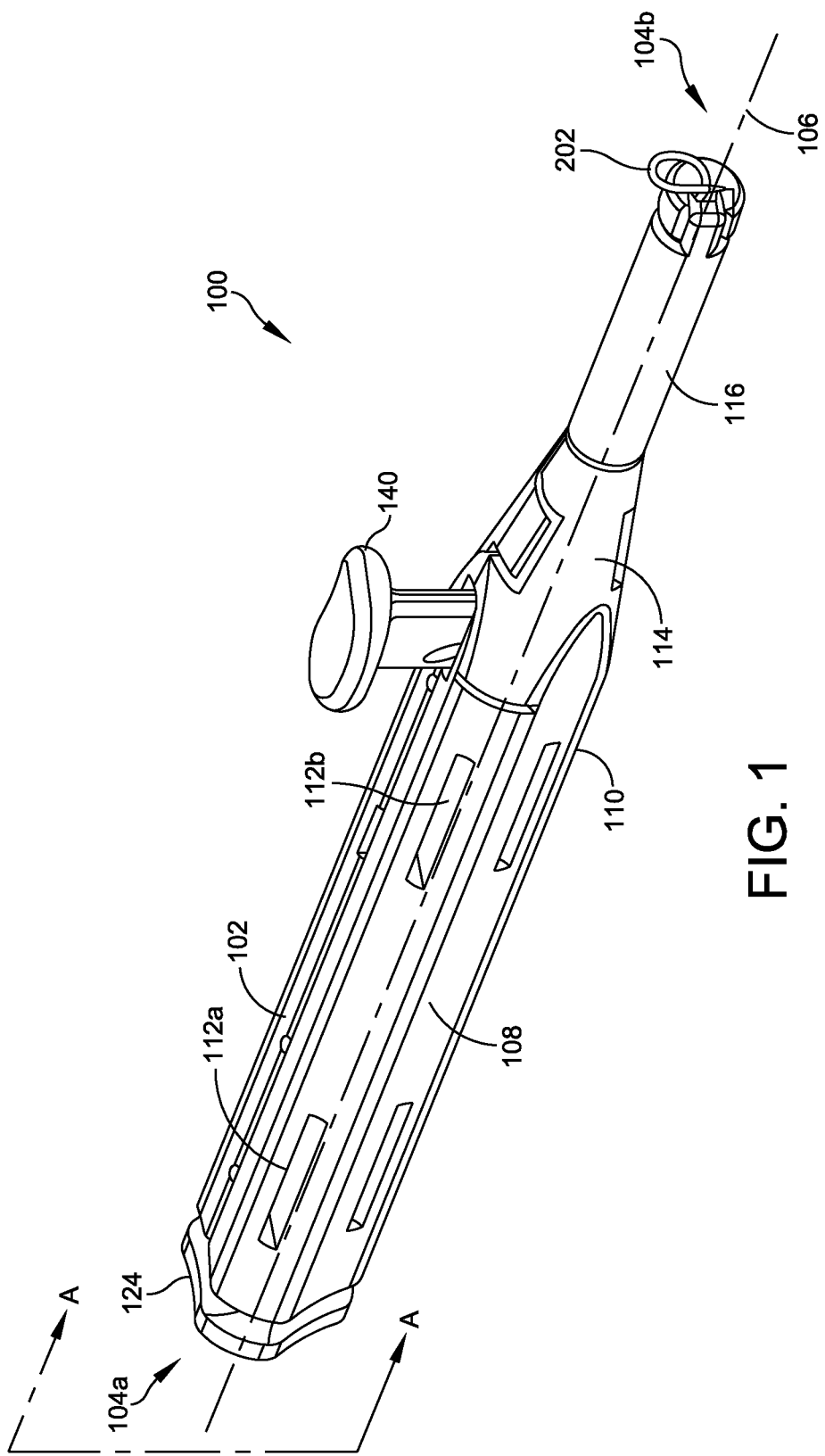
FIG. 1 illustrates an isometric view of a driver, in accordance with some embodiments.
Figure 2:
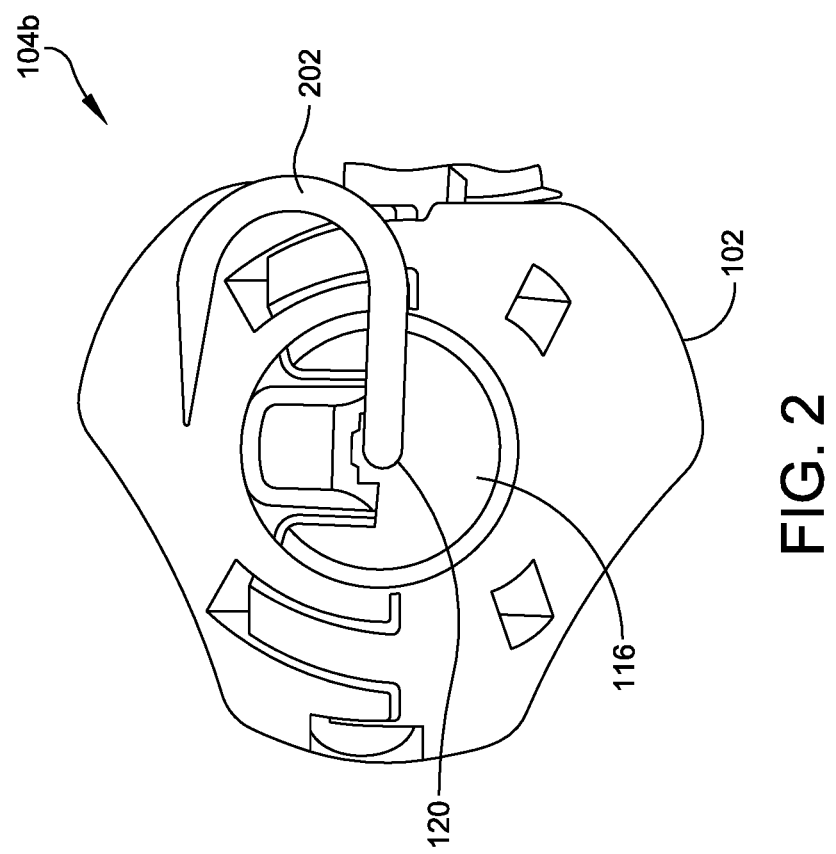
FIG. 2 illustrates a front view of the driver of FIG. 1, in accordance with some embodiments.
Figure 3:
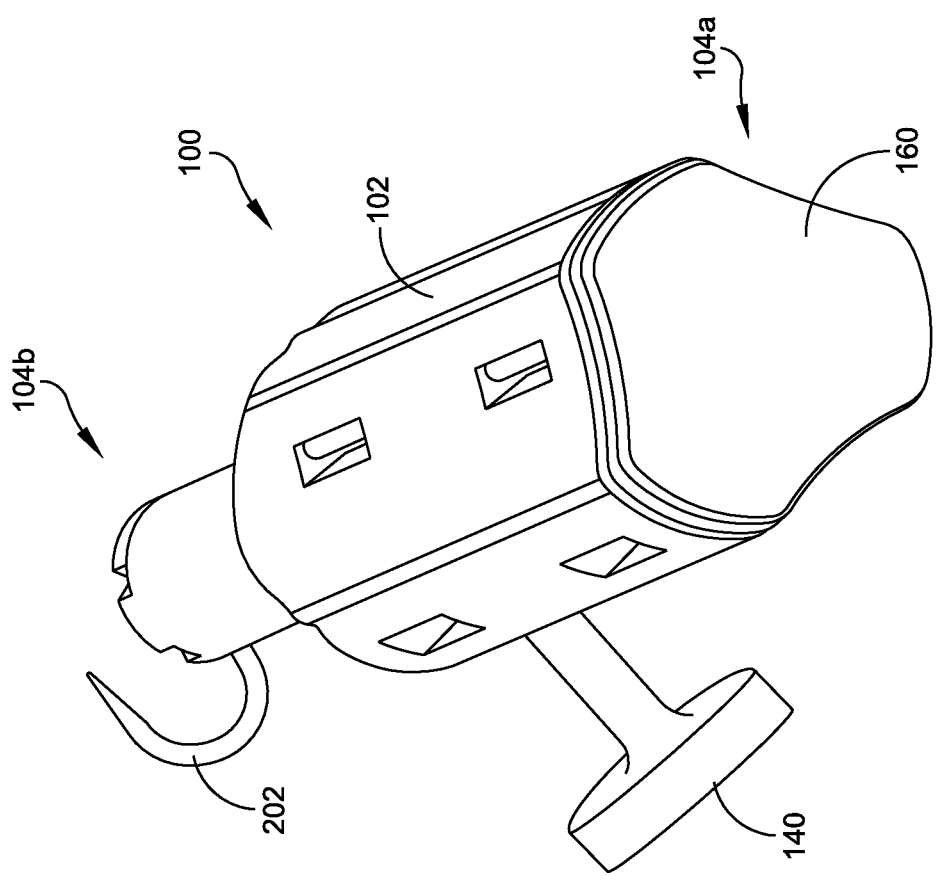
FIG. 3 illustrates a rear view of the driver of FIG. 1, in accordance with some embodiments.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top," "bottom," "proximal," "distal," "superior," "inferior," "medial," and "lateral" as well as derivative thereof (e.g., "horizontally," "downwardly," "upwardly," etc.) should be construed to refer to the orientation as then described or as shown in the drawing under discussion. For example, as used herein, the terms "dorsal," "plantar," "superior," and "inferior" are used herein to refer to the orientation of a bone in an anatomical position. The terms "dorsal" and "superior" and the terms "plantar" and "inferior" are equivalent as used herein. Similarly, the terms "proximal" and "distal" are used herein to refer to a position of a surgeon when holding a tool and/or position orientation of a bone in an anatomical position. These relative terms are for convenience of description and do not require that the apparatus be constructed or operated in a particular orientation. Terms concerning attachments, coupling and the like, such as "connected," refer to a relationship wherein structures are secured or attached to one another either directly or indirectly through intervening structures, as well as both movable or rigid attachments or relationships, unless expressly described otherwise.

In various embodiments, a system and method for soft tissue repair is disclosed. The system includes one or more instruments for inserting, retrieving, and/or manipulating a flexible strand, such as a driver, a needle, a strand retriever, and/or additional elements. The driver includes a body extending along a longitudinal axis from a proximal end to a distal end. The body defines a cavity therein. A distal end of the body defines a needle opening having a non-circular cross-section that is sized and configured to receive a mating portion of a needle therein. A first portion of the body extends from the distal end towards a neck and has a first diameter and a second portion of the body extends from the neck to a proximal end and has a second diameter. A needle is inserted into the non-circular needle opening in the distal end. The needle includes a non-circular mating portion having a complimentary cross-section with respect to the needle opening in the distal end of the body. The non-circular cross-section of the needle opening and the non-circular mating portion of the needle maintain the needle in a fixed position with respect to the driver and transfer a torsional force from the driver to the needle.

In various embodiments, the system includes a strand retriever. The strand retriever includes a body defining an inner cavity. A first longitudinal tube and a second longitudinal tube each extend from a first side of the body. A first snare and a second snare are slideably deployable from respective first and second longitudinal tubes. The first and second snares are deployable by a sliding deployment mechanism from a first position, in which each of the first snare and the second snare are substantially positioned within respective first and second longitudinal tubes, to a second position, in which the first snare and the second snare are substantially positioned distally of respective first and second longitudinal tubes. The first and second snares each include a loop sized and configured to receive a flexible strand therethrough.

In various embodiments, a method of soft tissue repair is disclosed. The method includes accessing and distracting a joint, such as a metatarsophalangeal (MTP) joint. A first flexible strand is passed through a first tissue section by a first needle coupled to a first driver. The first flexible strand extends into a cavity defined in the longitudinal body and is maintained in a fixed position with respect to the longitudinal body of the first driver. A second flexible strand can be coupled to the soft tissue section by a second needle coupled to a second driver. A first hole and a second hole are formed through a bone of the joint. The first flexible strand is passed through the first hole and the second flexible strand is passed through the second hole using a strand retriever. The first tissue section is secured to the bone using the first and second flexible strands.

FIGS. 1-7 illustrate a driver 100, in accordance with some embodiments. The driver 100 includes a body 102 extending from a proximal end 104a to a distal end 104b along a longitudinal axis 106. In some embodiments, the body 102 includes a handle portion 108 defined by a sidewall 110. The handle portion 108 can define one or more grooves (or openings) 112a, 112b. The grooves 112a, 112b define gripping sections of the handle portion 102. The handle portion 108 can define any suitable shape, such as a triangular shape, a circular shape, a rectangular shape, and/or any other suitable shape. The handle portion 108 has first radius (or width).

In some embodiments, the body 102 includes a neck 114 and an insertion portion 116. The neck 114 is coupled to the handle portion 108 at a proximal end and is coupled to the insertion portion 116 at a distal end. The insertion portion 116 extends from the neck portion along the longitudinal axis 106. The insertion portion 116 has a second radius (or width). In some embodiments, the second radius is less than the first radius. The neck portion 114 can be tapered from the first width at the proximal portion to the second width at the distal portion. In some embodiments, the neck 114 has a constant taper, although it will be appreciated that the neck 114 can have a variable taper and/or can be non-tapered. In some embodiments, each of the body 102, the neck 114, and the insertion portion 116 are concentric about the longitudinal axis 106, although it will be appreciated that one or more of the body 102, neck 114, or insertion portion 116 can be offset.

Figure 4:
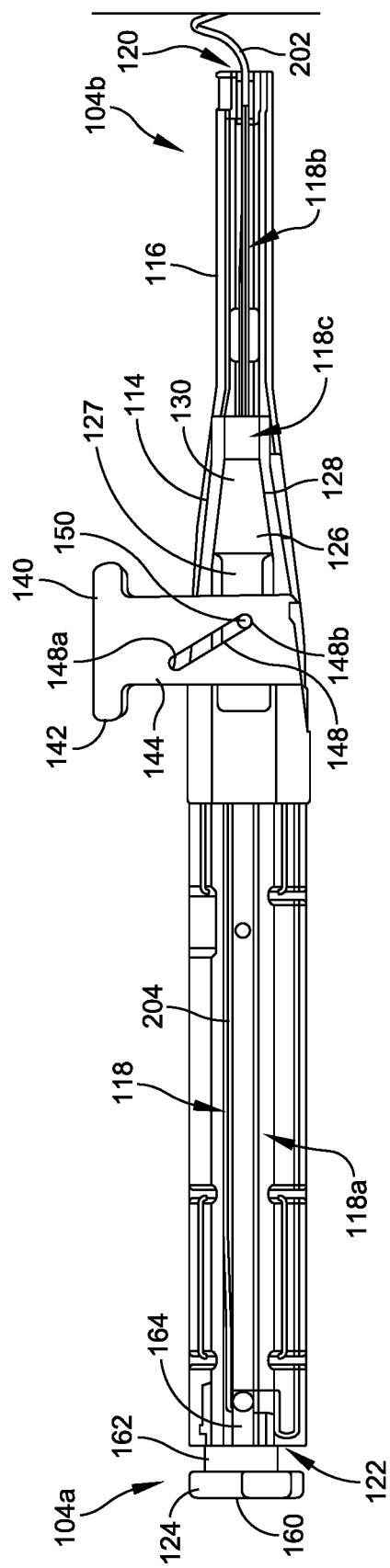
FIG. 4 illustrates a cross-sectional view of the driver of FIG. 1 taken along line A-A in FIG. 1, in accordance with some embodiments.

As shown in FIG. 4, in some embodiments, the body 102 defines an internal channel 118 (or cannula) extending from the proximal end 104a to the distal end 104b of the body 102. The channel 118 can include a first portion 118a having a first diameter, a second portion 118b having a second diameter, and a tapered portion 118c tapered from the first diameter to the second diameter. In some embodiments, the first portion 118a is defined by the handle portion 108, the second portion 118b is defined by the insertion portion 116, and the tapered portion 118c is defined by the neck 114. In some embodiments, the first diameter is greater than the second diameter.

A distal end 104b of the body 102 defines a needle opening 120. The needle opening 120 extends from an outer surface of the body 102 into the internal channel 118. The needle opening 120 is sized and configured to receive a mating portion 220 of a needle 202 therein (as discussed in greater detail below). In some embodiments, the needle opening 120 has a non-circumferential cross-section configured to transfer a torsional force to the needle 202. For example, in some embodiments, the needle opening 120 includes an oval or curved-rectangle cross-section including sidewalls having a first length and top and bottom walls having a second length that is less than the first length. Although specific embodiments are discussed herein, it will be appreciated that the needle opening 120 can have any suitable shape configured to transition a driving force to a needle 202.

In some embodiments, a proximal end 104a of the body 102 defines a cap opening 122. The cap opening 122 extends from an outer surface of the body 102 into the first portion 118a of the cavity 118. The cap opening 122 is sized and configured to receive a cap 124 therein. The cap 124 can be coupled to the body 102 by any suitable coupling mechanism, such as an interference fit, a thread, and/or any other suitable coupling mechanism. The cap 124 is configured to be coupled to a flexible strand 204 extending from the needle 202. As discussed in greater detail below, the cap 124 can be removed during surgery to retract a suture after an initial deployment of the needle and/or suture.

Figure 5:
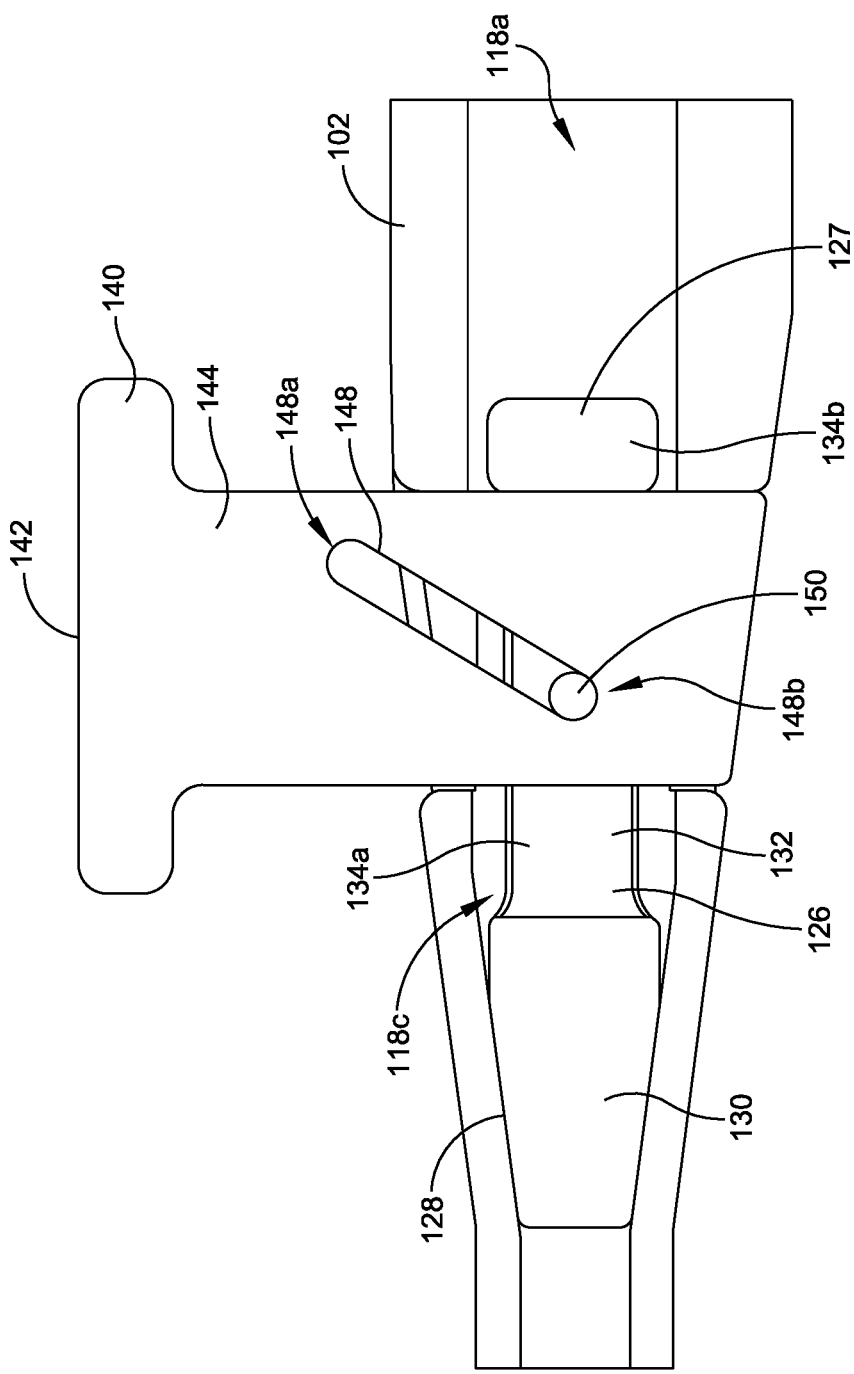
FIG. 5 illustrates a strand locking mechanism of the driver of FIG. 1 in a locked position, in accordance with some embodiments.

In some embodiments, a locking element 126 is disposed in the inner cavity 118. The locking element 126 is configured to maintain a needle in a fixed position with respect to the body 102. For example, the locking element 126 can include a locking body 127 configured to apply a force to the flexible strand 204. In some embodiments, the locking element 126 is configured to maintain the suture in a fixed position through a friction or interference fit between the locking body 127 and an inner surface 128 of the cavity 118. As shown in FIG. 5, in some embodiments, the locking element 126 includes a locking body 127 having a tapered head 130 sized and configured to be slideably received within the tapered portion 118c of the cavity 118. In some embodiments, the locking body 127 includes a semi-compressible or fully-compressible material disposed over at least a portion thereof. For example, in some embodiments, the locking body 127 includes a silicone and/or other material deposited over at least a portion of the locking body 127.

Figure 6:
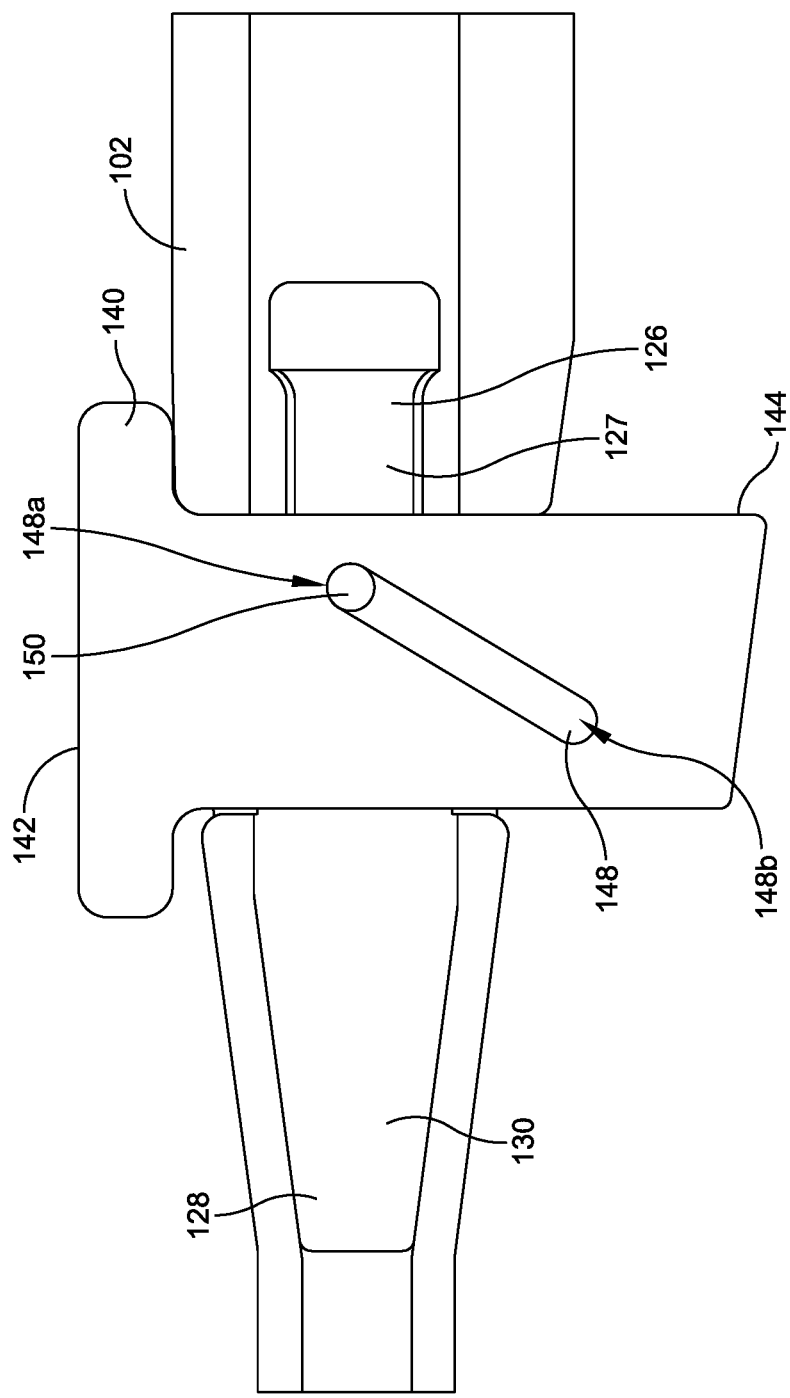
FIG. 6 illustrates the strand locking mechanism of FIG. 5 in an unlocked position, in accordance with some embodiments.

As shown in FIG. 6, when the locking body 127 is positioned distally within the tapered portion 118c, the tapered head 130 contacts the inner surface 128 of the cavity 118. The tapered head 130 and the inner surface 128 of the cavity 118 apply a frictional locking force to the flexible strand. The frictional locking force maintains the flexible strand 204 (and by extension the needle 202) in a fixed position with respect to the driver 100. When the locking body 127 is slidingly removed from the tapered portion 118c, the locking force is removed from the flexible strand and the flexible strand 204 and/or the needle 202 can be decoupled from the driver 100 through the needle opening 120.

In some embodiments, the locking element 126 includes a button 140 coupled to the locking body 127. The button 140 is configured to transition the locking body 127 from a first (or distal) position to a second (or proximal) position. In some embodiments, the button 140 includes a head 142 and a body 144 extending vertically therefrom. The body 144 defines a slot 148. The slot 148 extends through the body 140 at an angle between 0-90° with a proximal end 148a of the slot 148 located above a distal end 148b of the slot 148. The slot 148 is sized and configured to receive a pin 150. The pin 150 extends through the slot 148 and into the locking body 127. In some embodiments, the button 140 defines a channel extending through the vertical body 144 sized and configured to receive a portion of the locking body 127 therethrough.

In some embodiments, the locking body 127 includes a tapered head 130 having a complimentary taper with the tapered surface 118c of the cavity. The tapered head 130 is coupled to a longitudinal body 132 having a first portion 134a sized and configured for insertion through the channel formed in the button 140 and a second portion 134b sized and configured to abut a proximal surface of the button 140. Movement of button 140 in a direction perpendicular to the longitudinal axis of the locking body 127 (i.e., in an up/down direction), causes the locking body 127 to move longitudinally with respect to the driver body 102 such that the tapered head 130 is advanced into and/or out of contact with the inner surface 128 of the tapered portion 118c of the cavity 118.

In some embodiments, the slot 148 exerts a force on the pin 150 to translate the locking body 127 from a first, or distal, position to a second, or proximal, position. In the first position, a portion of the locking body 127 positioned within the tapered portion 118c of the inner cavity 118 and is in contact with an inner surface 128. In the second position, the locking body 127 is positioned substantially within the first portion 118a of the inner cavity 118 and is not in contact with the inner surface 128. In some embodiments, translation of the button from a locked (or upper) position to an unlocked (or lower) position transitions the locking body 127 from the first position to the second position. When the button 140 is in a locked position, as shown in FIG. 5, the pin 150 is positioned at a distal end 148a of the slot 148 and the head 130 of the locking body 127 is positioned within the tapered portion 118c of the cavity. The head 130 is tapered to provide a taper-taper friction interface between the head 130 and the tapered portion 118c to maintain the flexible strand 204 in a fixed position. When the button 140 is transitioned to the second position, as shown in FIG. 6, the slot 148 drives the pin 150 proximally, which moves the locking body 127 proximally. When the button 140 is fully depressed (i.e., in the second position), the pin 150 is located at a proximal end 148a of the slot 148 and the head 130 is spaced apart from the inner surface 128 of the cavity 118. The flexible strand 204 is able to freely move when the locking body 127 is in the second position (i.e., substantially located in the first portion 118a of the cavity 118).

Figure 7:
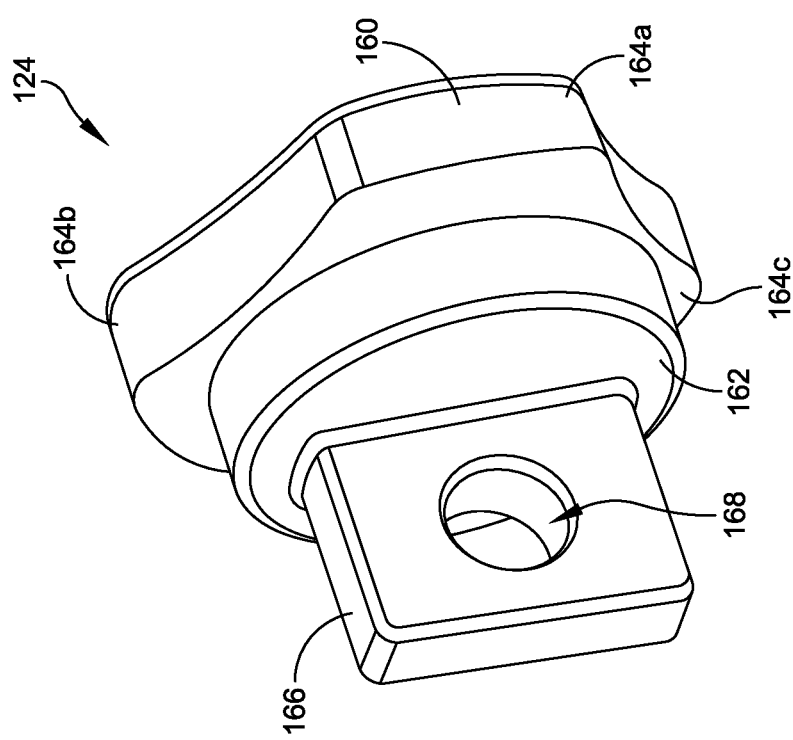
FIG. 7 illustrates a cap of the driver of FIG. 1, in accordance with some embodiments.

FIG. 7 illustrates a cap 124 sized and configured to be received within the cap opening 122 in a proximal end 104 of the body 102. The cap 124 includes a head 160 having a locking surface 162 extending therefrom. The locking surface 162 can include a conical and/or circular locking surface configured to couple the cap 124 within the cap opening 122 of the body 102. The locking surface 162 can be configured to provide a friction, interference, threaded, and/or other locking fit with the cap opening 122. The head 160 includes projections 164a-164c that extend circumferentially beyond the locking surface 162 and are configured to abut the proximal surface of the body 102 when the cap 124 is inserted into the cap opening 122. In some embodiments, the projections 164a-164c are configured to facilitate removal of the cap 124 from the cap opening 122.

In some embodiments, a boss 166 extends from the locking surface 162 and defines a hole 168 sized and configured to receive a flexible strand 204 therethrough. A proximal end of the flexible strand 204 is looped one or more times through the hole 168. When the needle 202 is deployed from the driver 100, the flexible strand 204 is pulled through the hole 166 such that the flexible strand 204 deploys from distal opening 120 without tangling. For example, the flexible strand 204 can be maintained in a taught and/or semi-taught state within the cavity 118 until a proximal end 218 of the flexible strand 204 passes through the hole 168. Once the proximal end 218 passes through the strand hole 168, the flexible strand 204 can be removed from the cavity 118 through the distal opening 120. In other embodiments, the flexible strand 204 can be maintained within the cavity 118 by any suitable mechanism, such as a spool, post, anchor, and/or any other suitable mechanism and/or can be freely moveable within the cavity 118.

In use, the driver 100 is configured to couple the needle 202 and the flexible strand 204 to a soft tissue section. During insertion of the needle 202, the driver 100 transfers a torsional force applied to the body 102 to the needle 202. The torsional force is transferred by an interaction between the non-circular proximal end 208 of the needle 202 and a non-circular cross-section of a needle opening 120 formed in the distal end 104a of the body 102. The torsional force drives the needle 202 through the soft tissue. As used herein, the term non-circular refers to any shape configured to prevent rotation of the needle 202 with respect to the needle opening 120, such as, an oval, ellipsoid, rectangular, triangular, non-regular, regular polygon, and/or any other suitable shape. Although embodiments are discussed herein including a transfer of torsional force, it will be appreciated that the driver 100 can be configured to transfer any suitable penetrating force from the driver 100 to the needle 202, such as a torsional force, a longitudinal force, etc.

After insertion of the needle 202 through the soft tissue, the button 140 is transitioned from the locked position to the unlocked position to disengage a locking element 126 from the flexible strand 204. After the locking element 126 is disengaged, the needle 202 and the flexible strand 204 can be removed through the distal opening 120 of the body 102. The needle 202 and/or the flexible strand 204 are configured to couple the soft tissue section to one or more structures, such as a bone, other soft tissue, a plate, and/or any other structure.

Figure 8:
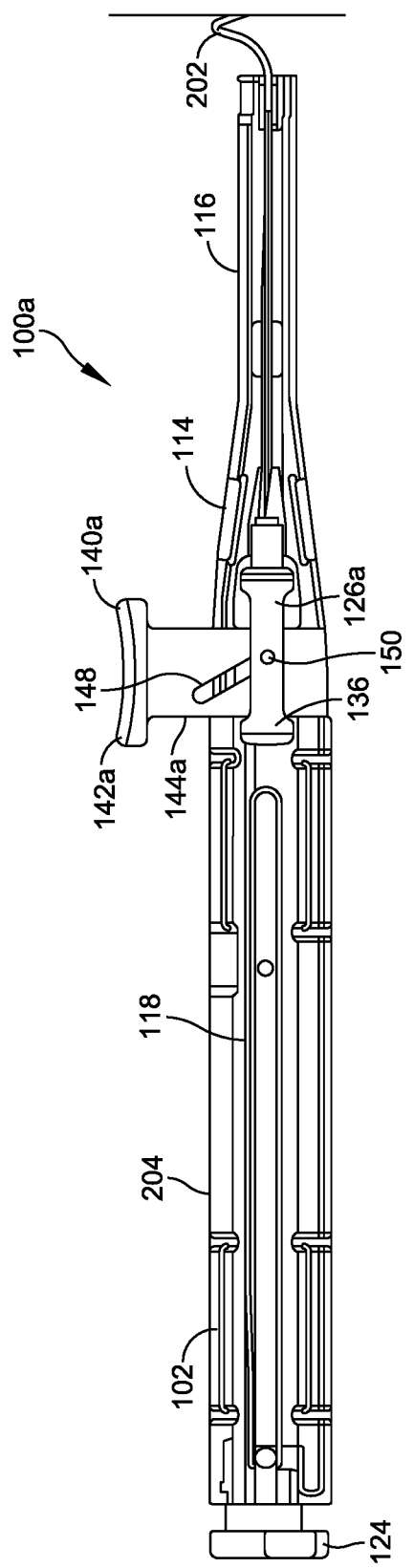
FIG. 8 illustrates a cross-sectional view of a driver including a compressible locking mechanism, in accordance with some embodiments.
Figure 10:
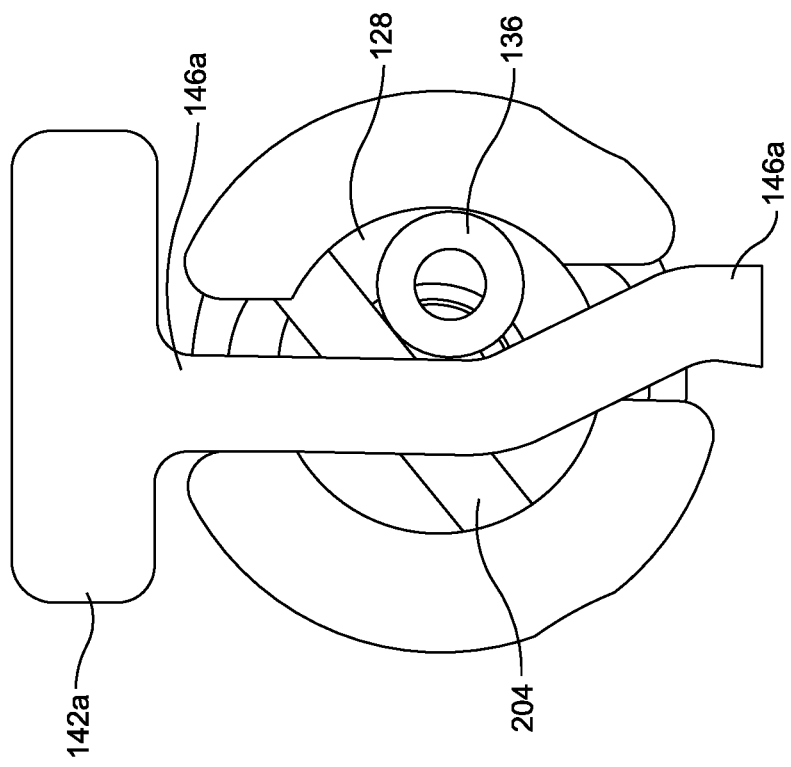
FIG. 10 illustrates the compressible locking mechanism of FIG. 8 in an unlocked position, in accordance with some embodiments.
Figure 9:
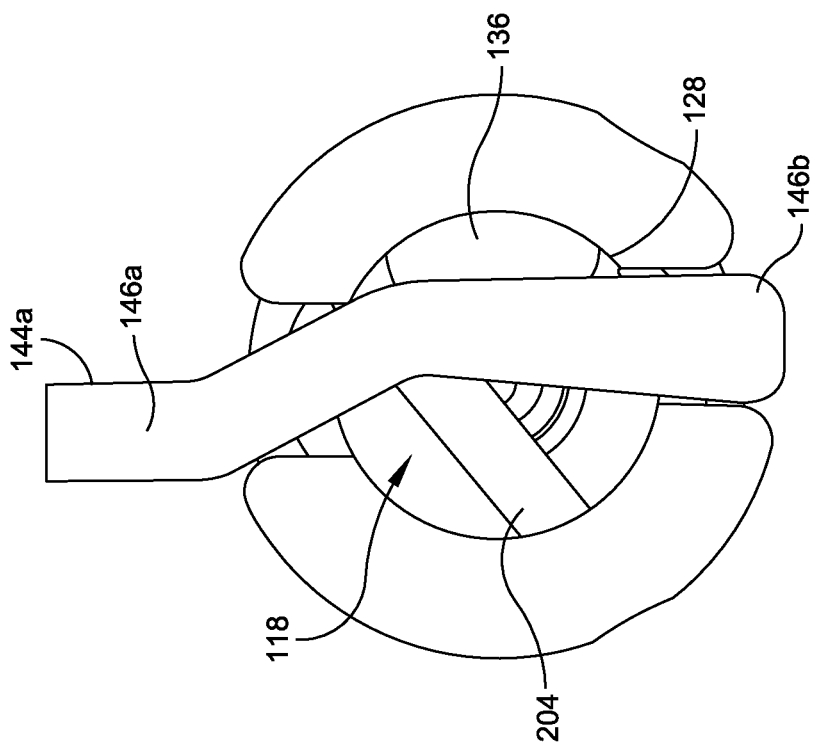
FIG. 9 illustrates the compressible locking mechanism of FIG. 8 in a locked position, in accordance with some embodiments.

FIGS. 8-10 illustrate an embodiment of a driver 100a including a compressible locking element 126a, in accordance with some embodiments. As shown in FIG. 8, the locking element 126a includes a compressible body 136, such as a flexible tube, configured to be deformed or compressed against the flexible strand 204 and the inner surface 128 of the cavity 118. A compression force is applied to the compressible body 136 (for example, by button 140a) which causes compression and deformation of the flexible tube 136, as shown in FIG. 9. The compressible body 136 applies a locking force to the flexible strand and maintains the flexible strand in a fixed position. The compressible body 136 returns to an un-compressed state (for example, a circular state) when the compressive force is removed, allowing the flexible strand to move freely within the cavity 118.

A button 140a is configured apply the compressive force to the compressible body 136 when in a locked position. For example, in some embodiments, the button 140a includes a head 142a and a body 144a extending therefrom. The body 144a includes a first vertical section 146a extending along a first vertical axis and a second vertical section 146b extending along a second vertical axis that laterally is offset from the first vertical axis.

In some embodiments, the button 140a is configured to be transitioned from the locked position to an unlocked position. In the locked position, the second section 146b is in contact with and compresses the compressible body 136, which applies the locking force to the flexible strand 204. The button 140a is transitioned from the locked position (shown in FIG. 9) to the unlocked position (shown in FIG.

10) to release the flexible strand 204 and/or an attached needle 202 from the driver. In the locked position, the second section 146b of the body 144a is positioned below and out of contact with the compressible body 136. The first section 146a is offset from the second section 146b such that when the button 140a is in the unlocked position, the first section 146a is adjacent to and spaced apart from the compressible body 136 at a distance sufficient to allow the compressible body 136 assume a non-deformed state.

In other embodiments, the locking element 126 can include a collet or other chuck-style locking element configured to lock the needle 202 both rotationally and longitudinally with respect to the body 102. The collet can include a three-piece chuck configured to lock the position of the needle 202. The collet can be positioned in any suitable portion of the driver 100, such as, for example, at the needle opening 120, within the neck 114, and/or at any other suitable portion of the driver 100.

Figure 12:
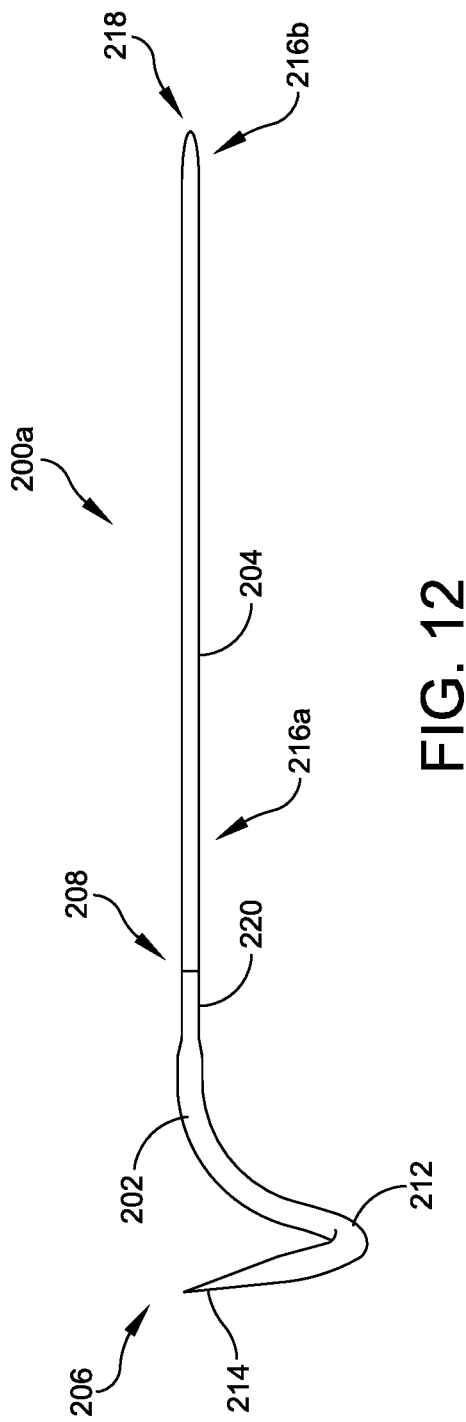
FIG. 12 illustrates a side view of the needle construct of FIG. 11, in accordance with some embodiments.
Figure 13:
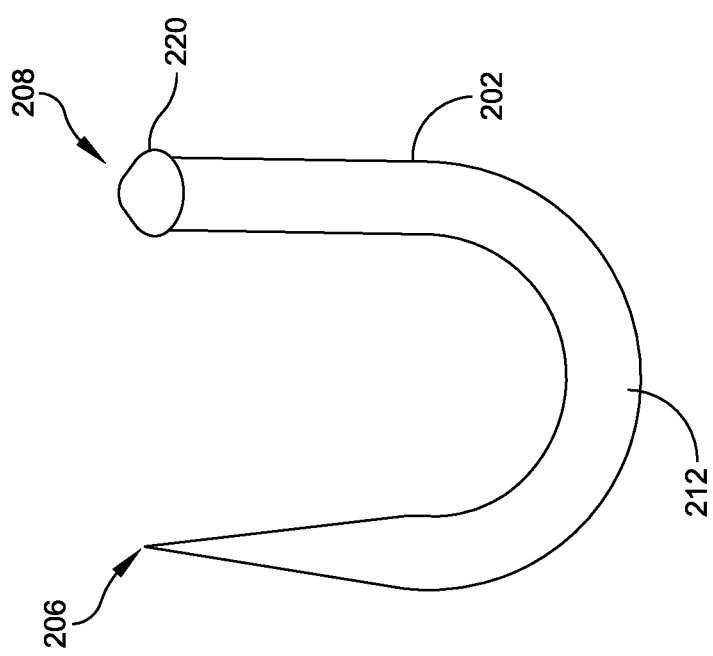
FIG. 13 illustrates a rear view of a needle of the needle construct of FIG. 11, in accordance with some embodiments.
Figure 14:
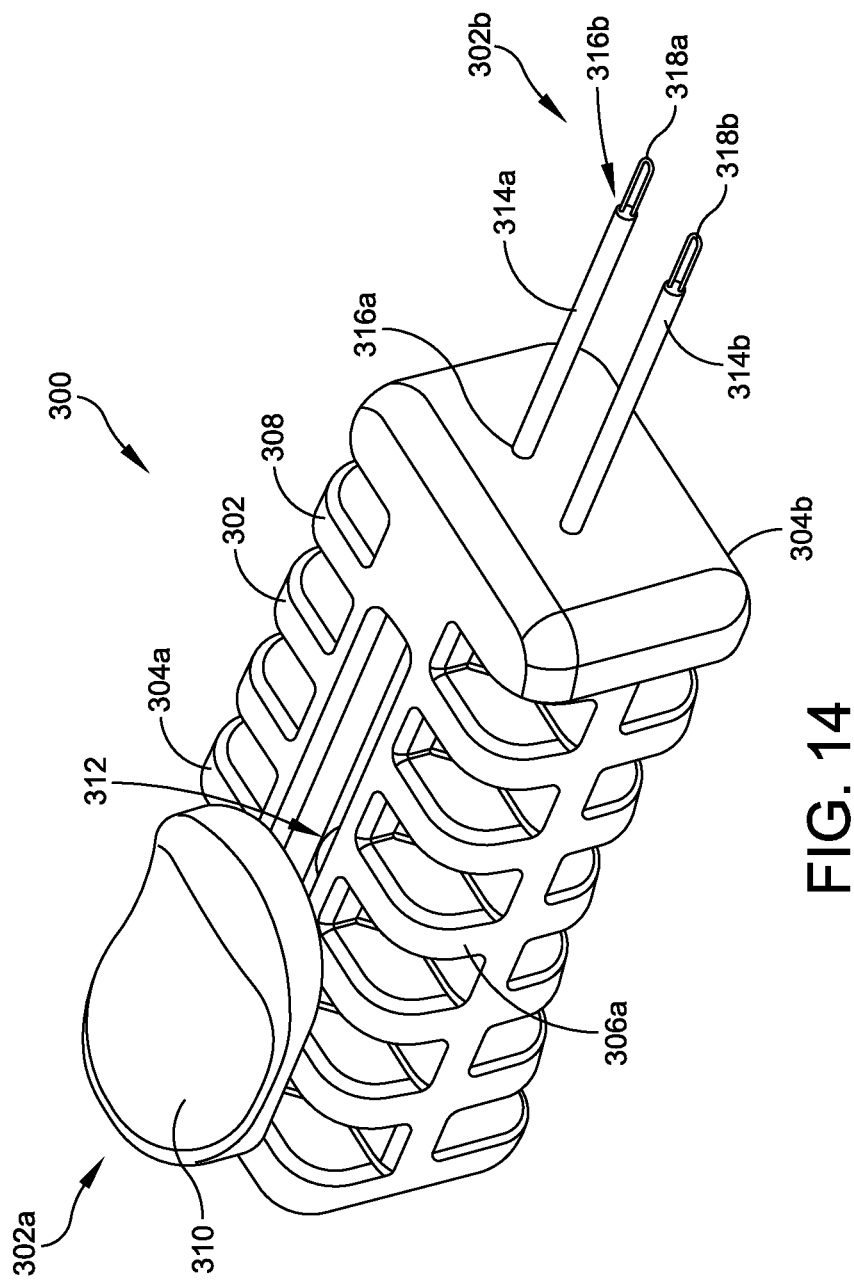
FIG. 14 illustrates an isometric view of a strand retriever, in accordance with some embodiments.
Figure 15:
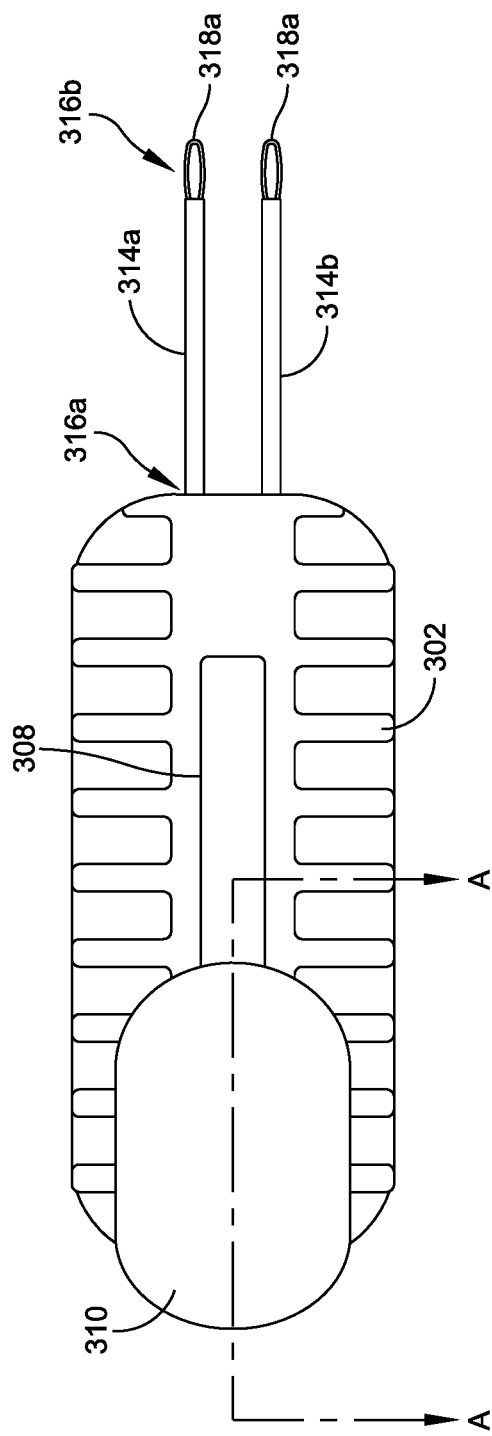
FIG. 15 illustrates a top view of the strand retriever of FIG. 14, in accordance with some embodiments.
Figure 16:
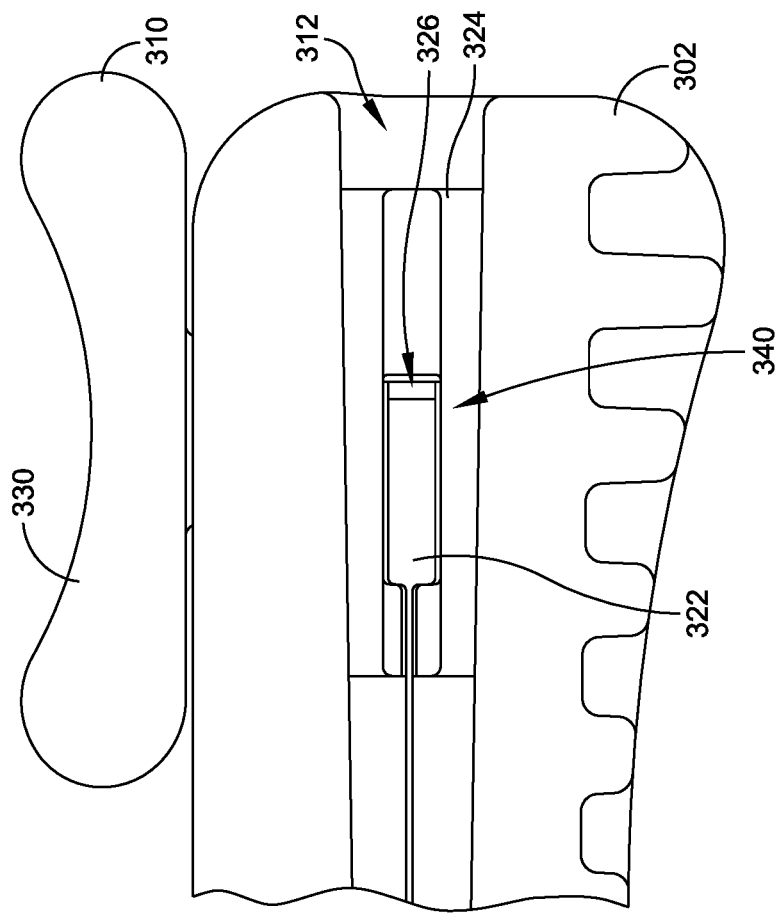
FIG. 16 is a cross-sectional view of the strand retriever taken along line A-A in FIG. 15, in accordance with some embodiments.
Figure 17:
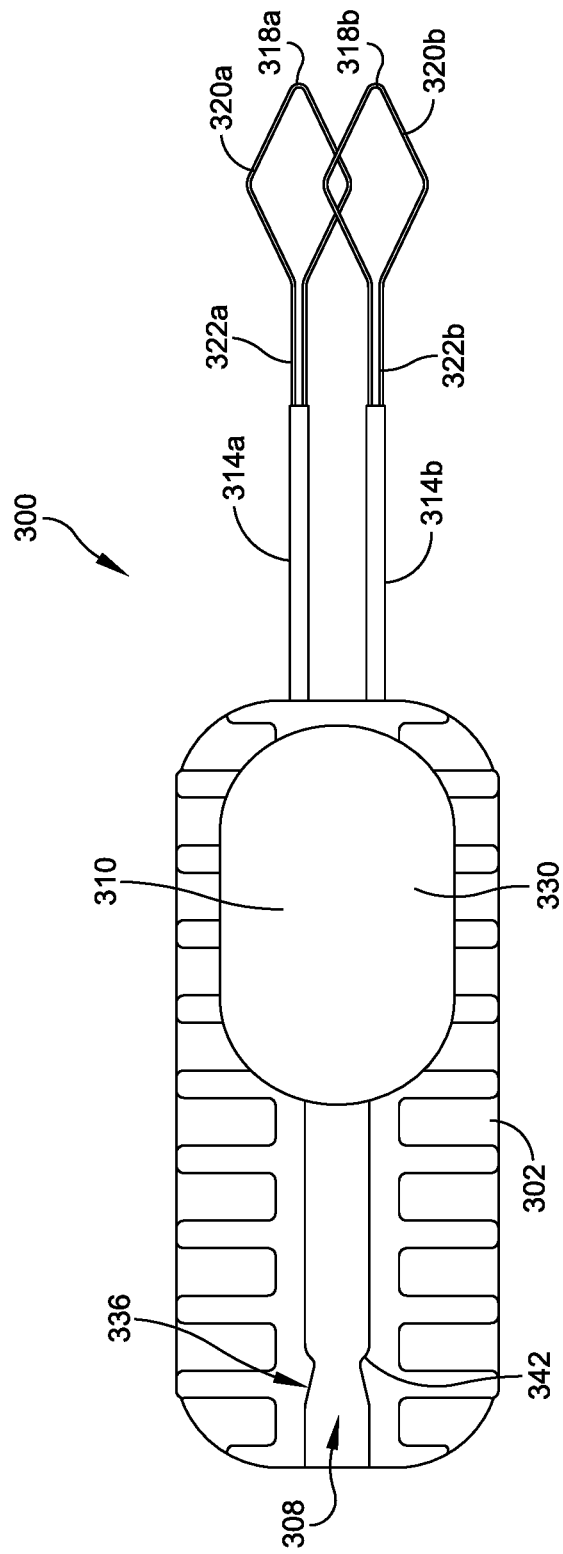
FIG. 17 illustrates the top view of the strand retriever of FIG. 14 having first and second snares in a deployed position, in accordance with some embodiments.
Figure 18:
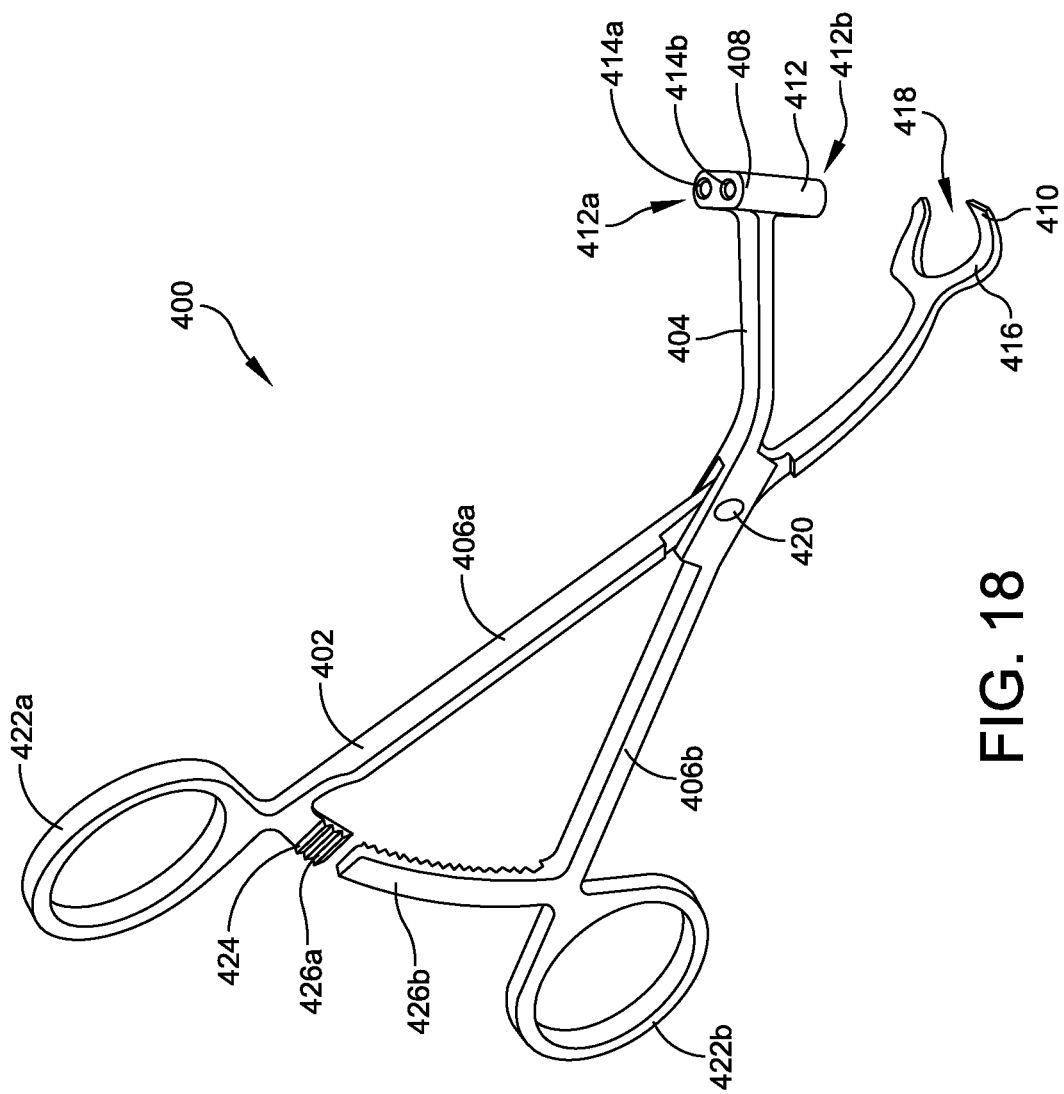
FIG. 18 illustrates an isometric view of a clamping drill guide, in accordance with some embodiments.
Figure 19:
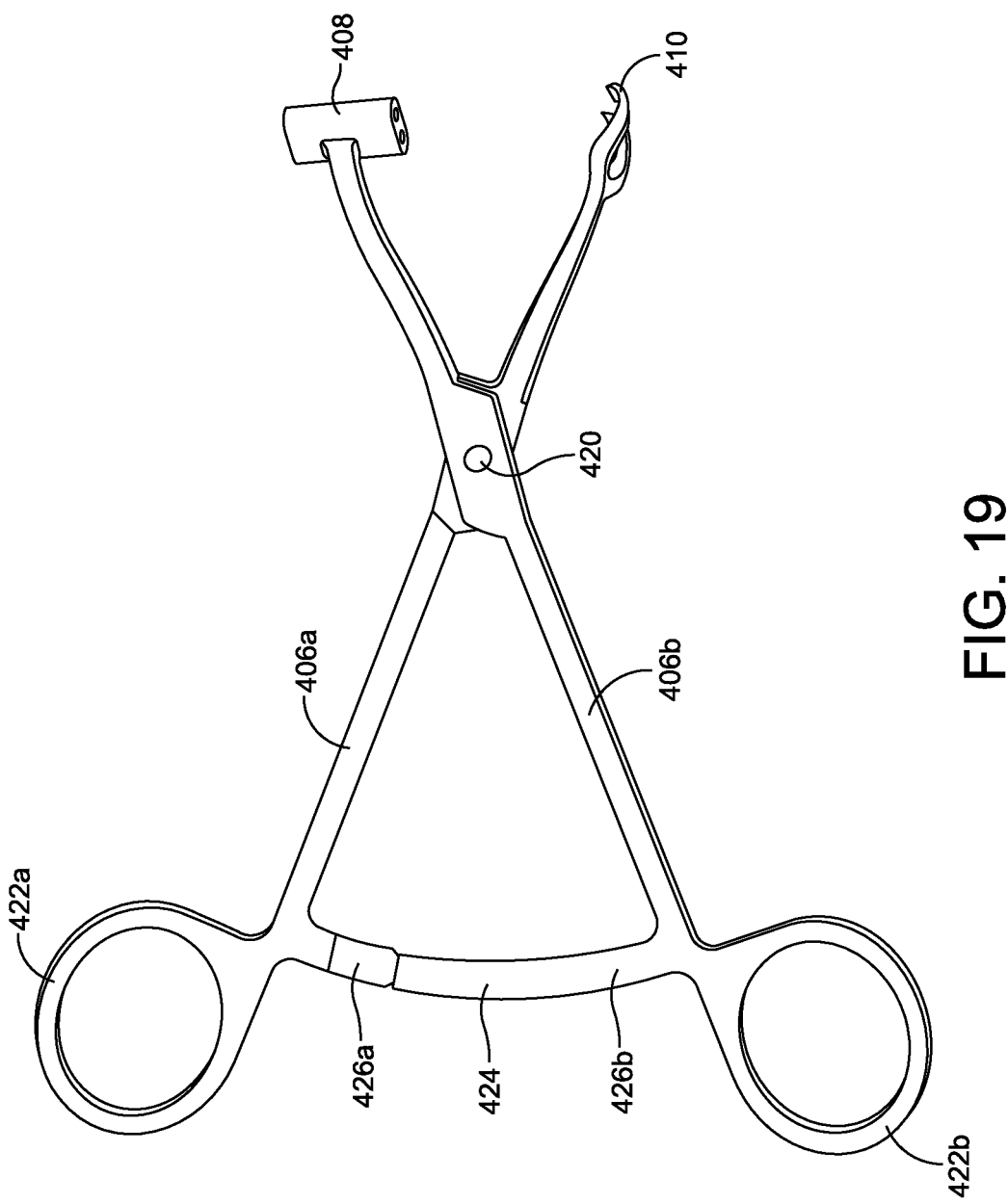
FIG. 19 illustrates a side view of the clamping drill guide of FIG. 18, in accordance with some embodiments.
Figure 20:
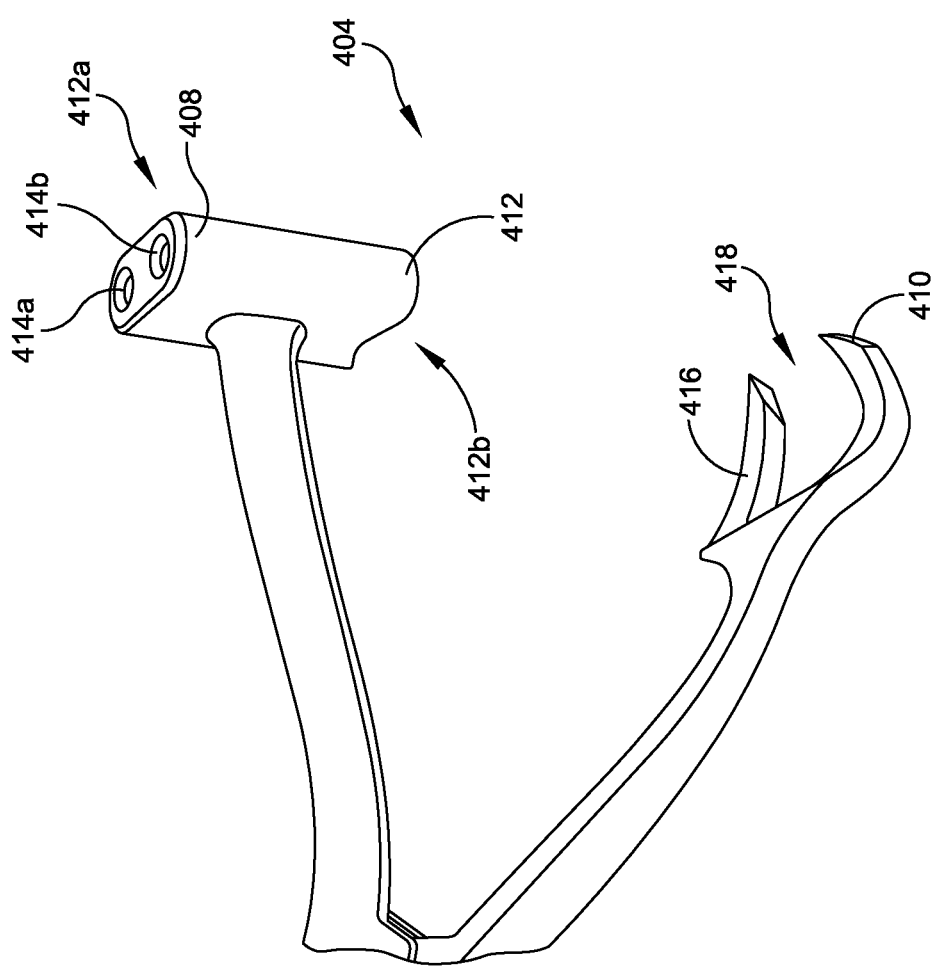
FIG. 20 illustrates a head of the clamping drill guide of FIG. 18, in accordance with some embodiments.
Figure 21:
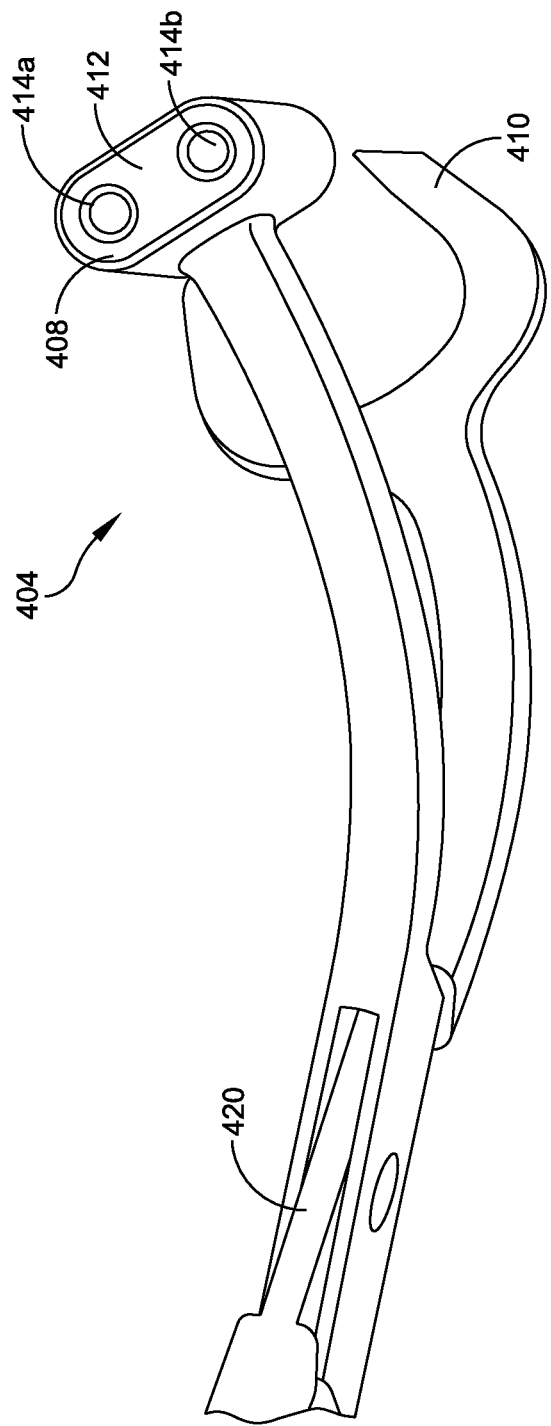
FIG. 21 illustrates a top view of the head of the clamping drill guide of FIG. 18, in accordance with some embodiments.

FIGS. 11-13 illustrate a needle construct 200 including a corkscrew needle 202 and a flexible strand 204 extending therefrom, in accordance with some embodiments. The corkscrew needle 202 includes a sharpened distal end 206, a non-circular proximal end 208, and a body 210 extending from the distal end 206 to the proximal end 208. The sharpened distal end 206 includes a sharpened tip 214 configured to penetrate tissue, such as a soft tissue section.

In some embodiments, the body 210 defines at least one helical turn 212 configured for rotational (or torsional) insertion of the needle 202 through a soft tissue section. In some embodiments, each helical turn 212 is configured to minimize tissue damage or trauma during insertion of the needle 202. For example, in some embodiments, pitch, arc length, and/or other elements of each helical turn 212 is configured to provide insertion of the needle 202 through a single hole formed in a soft tissue section by the sharpened distal end 206. Rotation of the needle 202, for example due to a torsional force applied to a driver 100, causes the helical turn 212 to pass through the single hole. Although embodiments are illustrated including a single helical turn, it will be appreciated that the needle 202 can include no helical turns (e.g., is straight and/or curved without a helical turn) or two or more helical turns in other embodiments.

In some embodiments, the proximal end 208 of the needle 202 defines a non-circular mating section 214. The non-circular mating section 214 is complimentary to the cross-section of the non-circular needle opening 120 formed in the driver 100. The non-circular mating section 214 is configured to receive a torsional force from the driver 100 and transfer the torsional force to the needle 202 during insertion of the needle 202 into a soft tissue section. The non-circular mating section 214 can have any shape complementary to the non-circular needle opening 120, such as, for example, an oval shape, a rectangular shape, a triangular shape, a regular geometric shape, an irregular geometric shape, and/or any other suitable shape As shown in FIGS. 11-12, the needle construct 200 includes a flexible strand 204 coupled to a proximal end 208 of the needle 202. The flexible strand 204 can be coupled to the needle 202 by any suitable coupling mechanism, such as a crimp engagement, a knot, and/or any other suitable coupling mechanism. For example, in the illustrated embodiment, the flexible strand 204 is coupled to the needle 202 by a crimp at a proximal end 208. In some embodiments, the coupling mechanism (such as a crimp) defines the non-circular mating section 214 of the needle 202.

The flexible strand 204 extends proximally from the needle 202. The flexible strand 204 can define a loop 216 extending from a distal end 216a to a proximal end 216b and/or can define one or more free ends at a proximal end 216b. In some embodiments, a proximal end 216b of the flexible strand 204 is coupled to a cap 124 of a driver 100. The flexible strand 204 is maintained in a semi-taught or taught state when positioned within the driver 100 to prevent knotting or other entanglement of the flexible strand 204 prior to insertion and release of the needle construct 200. The flexible strand 204 can include any suitable material, such as a suture, ribbon, wire, etc. In some embodiments, the flexible strand 204 can include a plurality of strands extending from a proximal end 208 of the needle 202 and each defining a free end and/or a loop configured to couple a soft tissue section to an anatomical and/or implanted structure.

FIGS. 14-17 illustrate a strand retriever 300, in accordance with some embodiments. The strand retriever 300 includes a body 302 extending from a proximal end 302a to a distal end 302b. The body 302 further extends between an upper surface 304a and a lower surface 304b and generally parallel side surfaces 306a, 306b. In some embodiments, the upper surface 304a defines a slot 308 sized and configured to receive a slideable deployment mechanism 310 therein. The slot 308 extends from a distal end 302b towards the proximal end 302a. In some embodiments, the slot 308 extends through the upper surface 304a to a cavity 312 defined by the body 302.

In some embodiments, at least one longitudinal tube 314a, 314b extends from the distal surface 302b of the body 302. The longitudinal tubes 314a, 314b each define a lumen extending from a proximal end 316a to a distal end 316b. In some embodiments, the longitudinal tubes 314a, 314b extend through the distal surface 302b of the body 302 such that the lumens defined therein are in communication with the cavity 312 defined by the body 302. In some embodiments, the longitudinal tubes 314a, 314b are parallel, although it will be appreciated that the longitudinal tubes 314a, 314b can be non-parallel in some embodiments. Although embodiments are illustrated having two longitudinal tubes 314a, 314b, it will be appreciated that the strand retriever 300 can include a greater and/or lesser number of longitudinal tubes, such as one longitudinal tube, three longitudinal tubes, etc.

In some embodiments, a first snare 318a is positioned within and slideably deployable from the first longitudinal tube 314a and a second snare 318b is positioned within and slideably deployable from the second longitudinal tube 314b. The first snare 318a and/or the second snare 318b each include a loop 320a, 320b coupled to a respective longitudinal shaft 322a, 322b extending proximally from the loop 320a, 320b. Each of the loops 320a, 320b can have any suitable circular and/or non-circular shape, such as a circumferential shape, a diamond shape, a rectangular shape, a triangular shape, an irregular shape, etc. In some embodiments, the loops 320a, 320b and/or the longitudinal shafts 322a, 322b are formed of a shape-memory material, such as a shape-memory metal (e.g., nitinol), although it will be appreciated that the loops 320a, 320b and/or the longitudinal shafts 322a, 322b can be formed of any resilient material. In some embodiments, each of snares 318a, 318b are formed of a single strand of material that defines the loop 320a, 320b and is comingled (e.g., twisted, braided, etc.) to form the longitudinal shaft 322a, 322b. In other embodiments, the loop 320a, 320b and the longitudinal shaft 322a, 322b are formed of separate strands (or materials) and are coupled together.

The first snare 318a and the second snare 318b are each slideably disposed within respective first longitudinal tube 314a and second longitudinal tube 314b. The first and second snare 318a, 318b are slideably deployed from a distal end 316b of the longitudinal tubes 314a, 314b by the sliding deployment mechanism 310. The first snare 318a and the second snare 318b are each formed of a resilient, shape-memory material configured to be compressed within the respective first and second longitudinal tubes 314a, 314b and that expands to define a respective loop 320a, 320b upon deployment from the longitudinal tubes 314a, 314b. The loops 320a, 320b are sized and configured to receive a needle 202 and/or a flexible strand 204 therethrough. In some embodiments, the loops 320a, 320b are configured to be compressed such that a first side of the loop 320a, 320b is parallel with a second side of the loop 320a, 320b in a compressed state.

In some embodiments, the first snare 318a and/or the second snare 318b are slideably deployable by the slideable deployment mechanism 310. The slideable deployment mechanism 310 includes a slider 330 positioned within the slot 308 and/or the cavity 312 defined in the body 302. The slider 330 is coupled to a body portion 324 defining a plurality of female slots 326 each configured to receive a crimped proximal end 340 of the longitudinal shaft 322a, 322b of a respective snare 318a, 318b therein, although it will be appreciated that any suitable engagement between the longitudinal shafts 322a, 322b and the slider 330 can be used. Although embodiments are discussed herein including a crimped proximal end 340, it will be appreciated that the longitudinal shafts 322a, 322b can be coupled to the slider 330 using any suitable method, such as, for example, crimping, over molding, injection molding, plasma welding, welding, adhesives, any other suitable coupling method and/or any combination thereof.

The slider 330 is longitudinally moveable within the slot 308 from a first (or proximal-most) position to a second (or distal-most) position. Translation of the slider 330 from the first position to the second position deploys the loops 320a, 320b of first and second snares 318a, 318b from respective first and second longitudinal tubes 314a, 314b. In some embodiments, a portion of the longitudinal shaft 322 of each of the snares 318a, 318b is also deployed from the first and second longitudinal tubes 314a, 314b such that the loops 320a, 320b are spaced apart from a proximal end 316a of a respective longitudinal tube 314a, 314b.

In some embodiments, the slot 308 includes a proximal locking feature 336 configured to maintain the slider 330 in a fixed proximal position prior to deployment of the snares 318a, 318b. For example, in some embodiments, the proximal locking feature 336 includes a proximal detent 342 formed in the slot 308. The locking feature 336 maintains the slideable deployment mechanism 310 (and the attached snares 318a, 318b) in a fixed proximal position until a predetermined force is applied to the slider 330 to force the slideable deployment mechanism 310 beyond the locking feature 336. In other embodiments, the locking feature 336 can include a spring-loaded locking feature, a hinged locking feature, and/or any other suitable locking feature. The locking feature 336 prevents deployment of the snares 318a, 318b prior to positioning of the strand retriever 300 during surgery.

FIGS. 18-22 illustrate a clamping drill guide 400, in accordance with some embodiments. The clamping drill guide 400 is configured to be securely coupled to (i.e., clamped to) a second bone. The clamping drill guide 400 is configured to guide insertion of a drill element to form one or more holes in the second bone. For example, in some embodiments, the clamping drill guide 400 is configured to guide formation of one or more holes through the second bone. The clamping drill guide 400 is further configured to guide insertion of one or more elements of a strand retriever 300, as discussed in greater detail below.

The clamping drill guide 400 includes a handle portion 402 and a head 404 coupled to the handle portion 402 by a pivoting connection 420. The handle portion 402 includes a first handle 406a and a second handle 406b coupled by the pivoting connection 420. Each of the handles 406a, 406b includes a finger loop 422a, 422b sized and configured to allow a user to grip and/or manipulate the handles 406a, 406b during surgery. The head 404 includes a guide element 408 coupled to the first handle 406a and a clamping element 410 coupled to the second handle 406b. The guide element 408 includes a body 412 defining at least one guide hole 414a, 414b extending from a first side 412a to a second side 412b of the body 412. In some embodiments, the guide holes 414a, 414b are parallel and extend through the body 412 parallel to a longitudinal axis of the body 412, although it will be appreciated that each of the guide holes 414a, 414b can be angled with respect to the longitudinal axis and/or with respect to the other guide hole 414a, 414b. The guide holes 414a, 414b are sized and configured to receive a hole forming element therethrough. For example, in various embodiments, the guide holes 414a, 414b can be configured to receive a drilling element (such as a drill bit), a k-wire, a cutting element, and/or any other suitable hole forming element therethrough.

The clamping element 410 includes a body 416 configured to apply a clamping force to a bone positioned between the clamping element 410 and the guide element 408. The body 416 defines an opening 418 aligned with the guide holes 414a, 414b such that a hole forming element inserted through the guide holes 414a, 414b passes through the opening 418 when the head 404 is in a clamped configuration. In some embodiments, the body 416 defines a first end 416a and a second end 416b spaced apart to define a slot, such as an open crescent or other open shape. The opening 418 is defined at least partially by a perimeter of the body 416 extending between the first end 416a and the second end 416b. In other embodiments, the body 416 defines a closed shaped and the opening 418 is defined entirely by an internal perimeter of the body 416, such as a circular closed shape, non-circular geometric shape, etc.

In some embodiments, the guide element 408 and the clamping element 410 are coupled in a hinged arrangement and are configured to receive a portion of a bone therebetween. For example, in some embodiments, the guide element 408 and the clamping element 410 define an adjustable opening therebetween sized and configured to receive a portion of a bone, such as a proximal phalanx, although it will be appreciated that the guide element 408 and the clamping element 410 can define a greater and/or lesser opening configured to receive alternative and/or additional bones.

In some embodiments, the clamping drill guide 400 includes a locking element 424 configured to maintain a fixed position of the first handle 406a and the second handle 406b during clamping of a bone. The locking element 424 includes a first locking element 426a coupled to the first handle 406a and a second locking element 426b coupled to the second handle 406b. The first and second locking elements 426a, 426b are coupled together to provide a variable clamping force to a bone and maintain the handles 406a, 406b in a fixed position.

Figure 22:
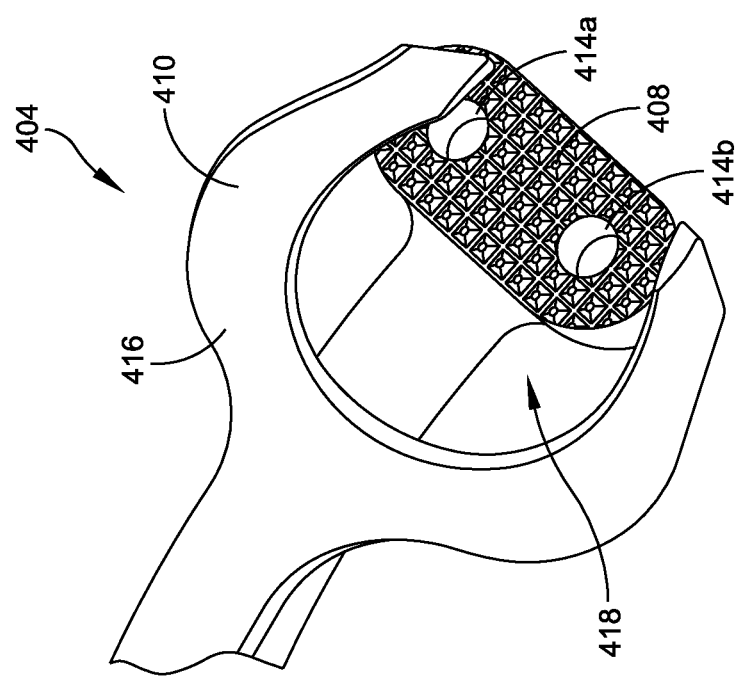
FIG. 22 illustrates a bottom view of the head of the clamping drill guide of FIG. 18, in accordance with some embodiments.

As illustrated in FIG. 22, in some embodiments, a bone-facing surface 412b of the guide element 408 defines a textured surface. The textured surface is configured to provide increase friction between the guide element 408 and the bone when the clamping drill guide 400 is coupled to the bone. The textured surface can be any suitable textured surface, such as a plasma coated surface, a laser etched surface, a knurled surface, a surface including one or more protrusions (such as machined-in protrusions), and/or any other suitable textured surface.

Figure 23:
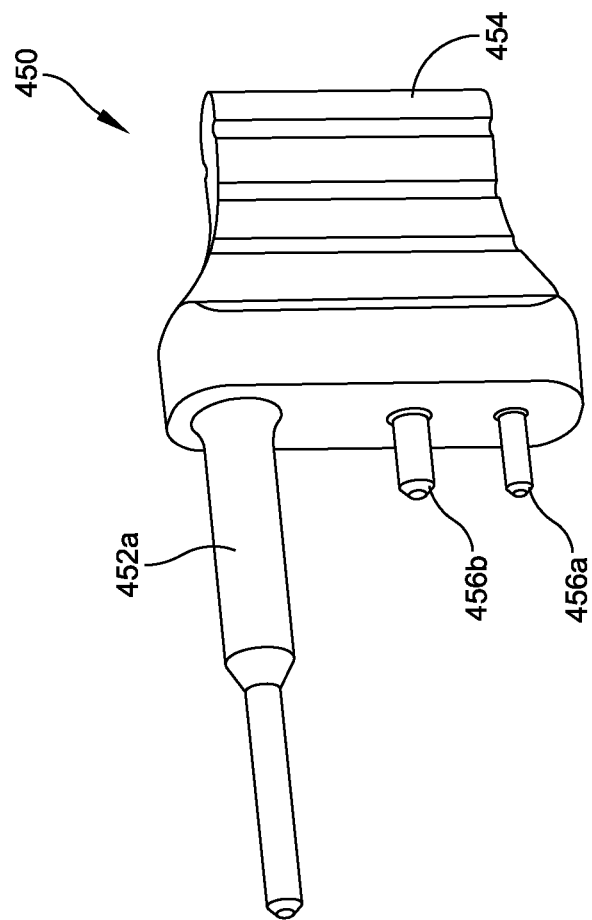
FIG. 23 illustrates a drill trajectory guide configured to be coupled to the clamping drill guide of FIG. 18, in accordance with some embodiments.

FIG. 23 illustrates a trajectory guide 450 configured to be coupled to the head 404 of the clamping drill guide 400, in accordance with some embodiments. The trajectory guide 450 includes a first post 452 extending from a body 454. The post 452 is configured to indicate a path of a hole forming element when the trajectory guide 450 is coupled to the clamping drill guide 400. For example, in some embodiments, when viewed sagittally, a post 452 indicates a path of a drill guide 414a, 414b. The trajectory guide 450 indicates the path of the drill guide holes 414a, 414b to verify that a hole forming element inserted through the guide element 408 does not violate undesirable soft tissue and/or bone surfaces, such as an articular surface of a phalanx. In some embodiments, the trajectory guide 450 includes one or more pins 456a, 456b sized and configured for insertion into the guide holes 414a, 414b formed in the guide element 408. The pins 456 align the trajectory guide 450 with the guide element 408 and maintain the trajectory guide 450 in a fixed position.

Figure 24:
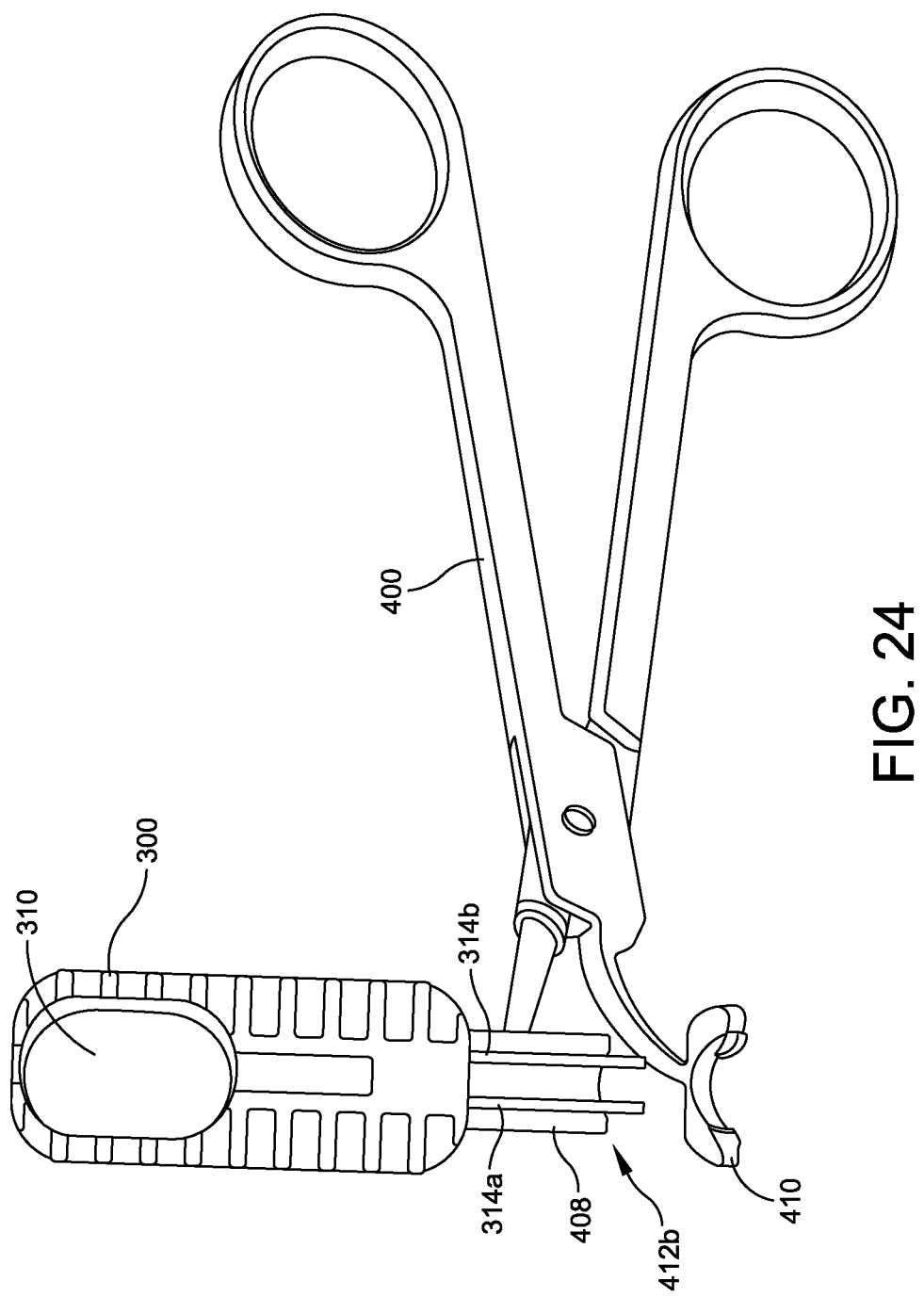
FIG. 24 illustrates a strand retriever coupled to a clamping drill guide, in accordance with some embodiments.
Figure 25:
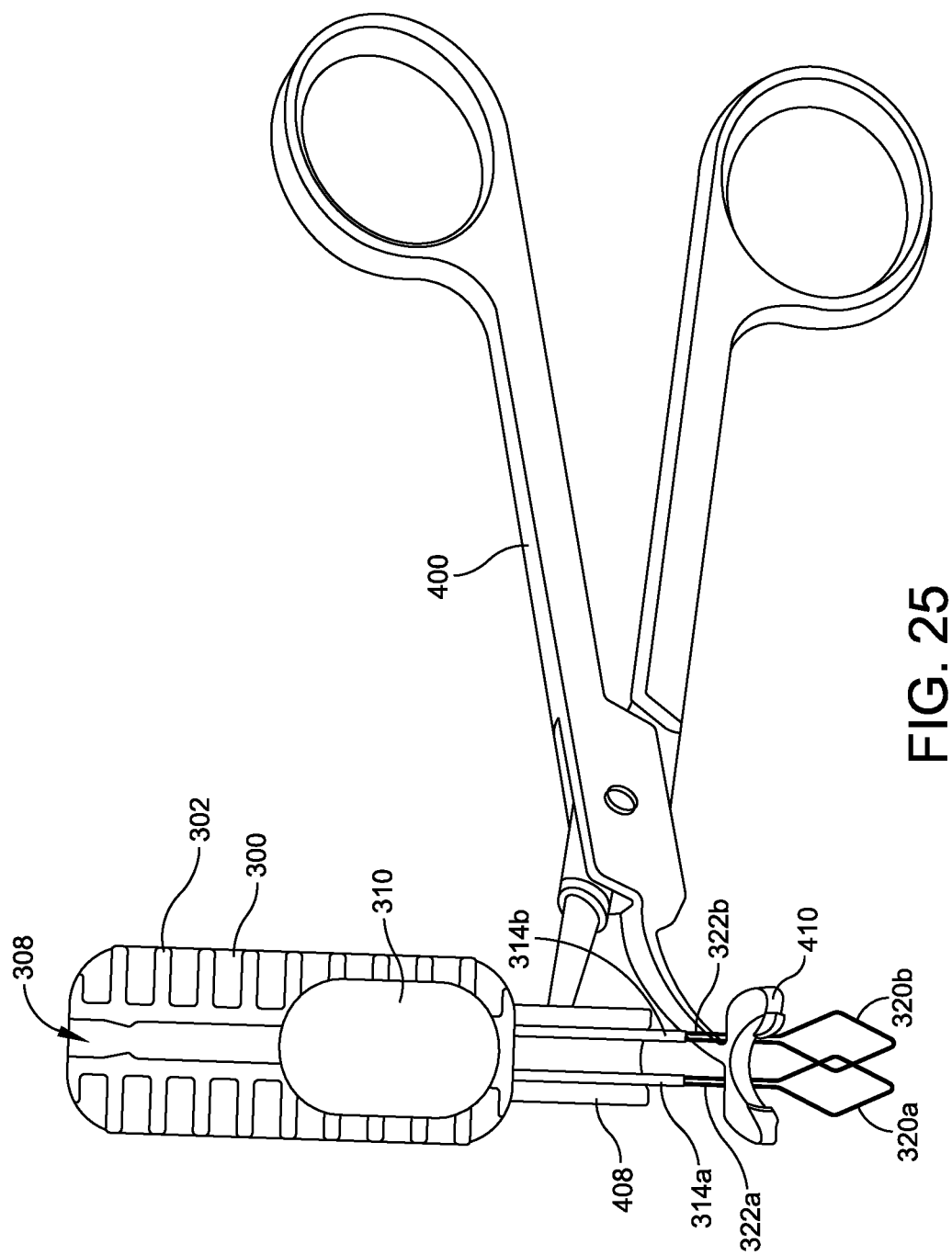
FIG. 25 illustrates deployment of first and second snares of the strand retriever of FIG. 24 through the clamping drill guide, in accordance with some embodiments.

FIG. 24 illustrates a strand retriever 300 having longitudinal tubes 314a, 314b and/or the snares 318a, 318b inserted through the guide holes 414a, 414b of the clamping drill guide 400. The longitudinal tubes 318a, 318b have an outer diameter less than a diameter of the guide holes 414a, 414b. The longitudinal tubes 318a, 318b extend at least partially into the guide holes 414a, 414b. In some embodiments, the longitudinal tubes 318a, 318b extend beyond a distal end 412b of the guide body 412.

The snares 318a, 318b of the strand retriever 300 are deployed from the longitudinal tubes 314a, 314b after insertion of the longitudinal tubes 314a, 314b into the guide holes 414a, 414b. In some embodiments, the longitudinal shaft 322a, 322b of each of the snares 318a, 318b has a length sufficient to position the respective loops 320a, 320b of each of the snares 318a, 318b distal of the clamping element 410 of the clamping drill guide 400. For example, in the illustrated embodiment, the longitudinal shaft 322a, 322b of each of the snares 318a, 318b positions a proximal end of the loop 320a, 320b beyond the clamping element 410. The loops 320a, 320b are fully expanded when positioned distal of the clamping element 410. Because the loops 320a, 320b are substantially contained within the longitudinal tubes 314a, 314b during deployment, the flexibility of the loops 320a, 320b does not hinder deployment through the clamping drill guide 400.

In some embodiments, the guide holes 414a, 414b are configured to deploy the snares 318a, 318b through the opening 418 defined by the clamping element 410. For example, in some embodiments, the loops 320a, 320b and/or the longitudinal shafts 322a, 322b of each of the snares 318a, 318b are configured to pass through the opening 418 when deployed from the strand retriever 300. The loops 320a, 320b are positioned distal of the clamping element 410 and expand after passing at least partially through the opening 418.

Figure 26:
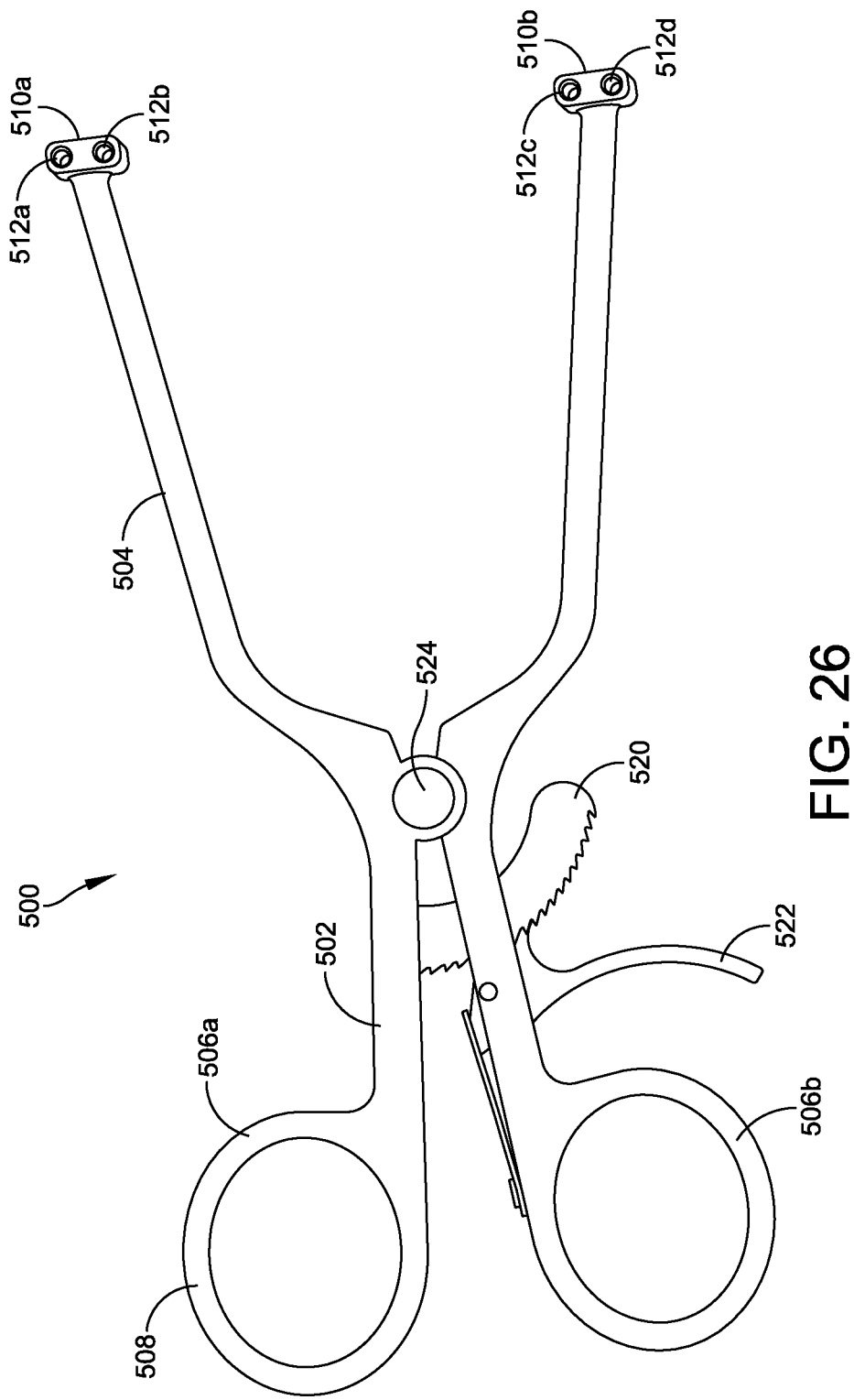
FIG. 26 illustrates a top view of a joint distractor, in accordance with some embodiments.

FIG. 26 illustrates a joint distractor 500, in accordance with some embodiments. The joint distractor 500 includes a proximal portion 502 and a distal portion 504. The proximal portion 502 includes a first handle 506a and a second handle 506b coupled in a pivoting arrangement by pivoting element 524. The first handle 506a and the second handle 506b each define a finger loop 508 configured to allow a user to grip the hands 506a, 506b and/or actuate the handles 506a, 506b.

In some embodiments, the proximal portion 504 includes a first anchoring body 510a coupled to the first handle 506a and a second anchoring body 510b coupled to the second handle 506b. Each of the first and second anchoring bodies 510a, 510b define at least one hole 512a-512d extending from a first end to a second end. For example, in the illustrated embodiment, a first hole 512a, 512c and a second hole 512b, 512d extend through the anchoring bodies 510a, 510b, although it will be appreciated that the anchoring bodies 510a, 510b can define a greater and/or lesser number of holes 512a-512d. The holes 512a-512d can extend through each of the respective anchoring bodies 510a, 510b along parallel and/or non-parallel axes.

Each of the holes 512a-512d are sized and configured to receive an anchoring element therein. For example, in some embodiments, each of the holes 512a-512d are sized and configured to receive a k-wire therethrough, although it will be appreciated that holes 512a-512d can be configured to receive any suitable anchoring element, such as a k-wire, a screw, a pin, and/or any other suitable anchoring element. Anchoring elements inserted through each of the holes 512a-512d are configured to anchor the respective anchoring body 510a, 510b to a tissue section, such as a bone section. After anchoring the anchoring bodies 510a, 510b to the bone section, the handles 506a, 506b can be actuated to separate the anchoring bodies 510a, 510b to distract the bone sections coupled to the respective anchoring body 510a, 510b.

In some embodiments, the joint distractor 500 includes a locking element 520. The locking element 520 is configured to lock the handles 506a, 506b at a selected length/distance corresponding to a selected distraction of the anchoring bodies 510a, 510b. In some embodiments, the locking element 520 includes a ratcheting locking element, although it will be appreciated that any suitable locking element can be used. In some embodiments, the locking element 520 includes a release 522.

Figure 27:
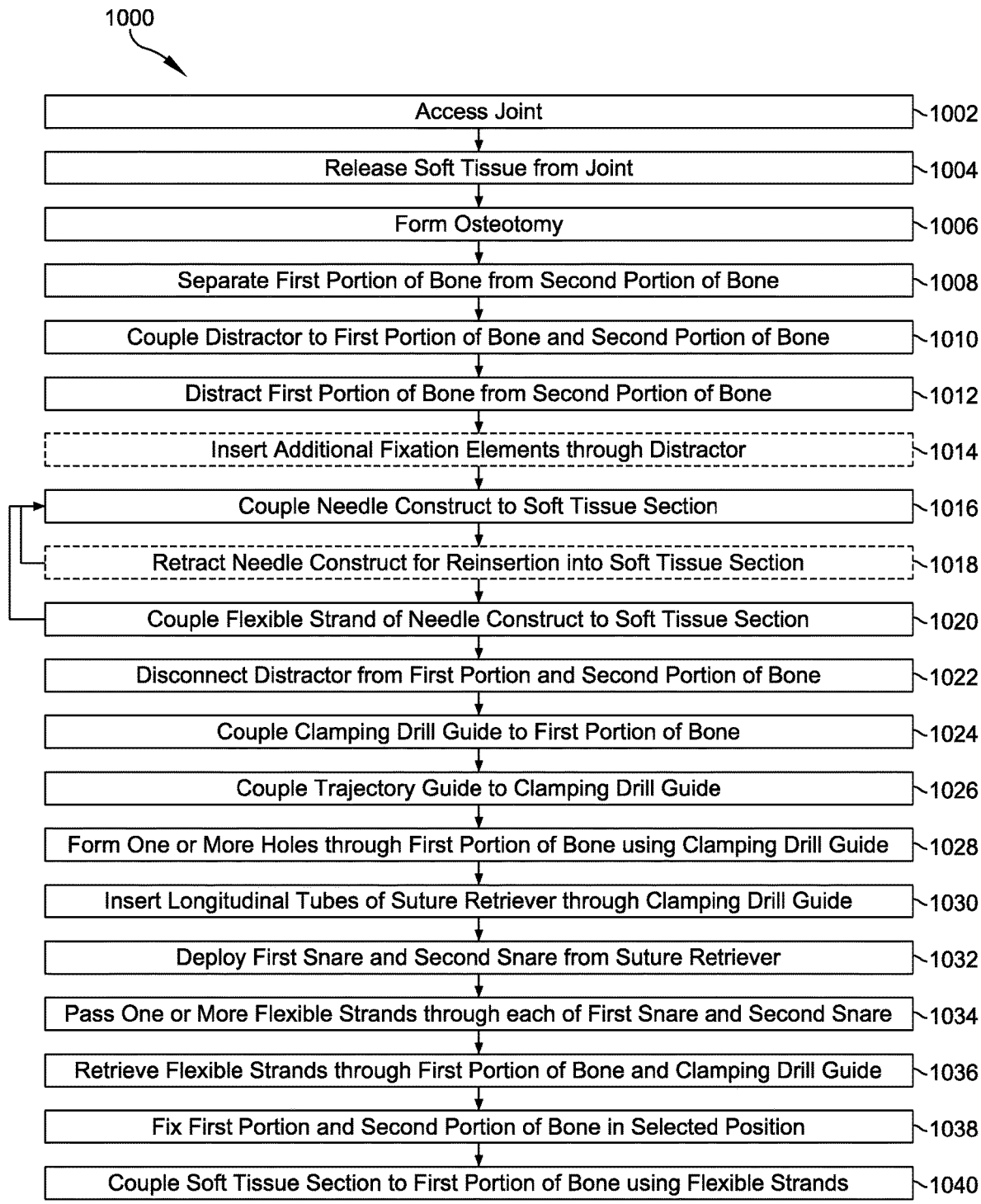
FIG. 27 illustrates a method of soft tissue repair, in accordance with some embodiments.

FIG. 27 illustrates a method 1000 of soft tissue repair and FIGS. 28-39 illustrate various steps of the method 1000, in accordance with some embodiments. At step 1002, an incision is formed to access a joint of a patient, such as a metatarsophalangeal (MTP) joint. Although embodiments are discussed herein with reference to an MTP joint, it will be appreciated that the method 1000 and/or the surgical instruments used during the method 1000 can be used for various joints and/or soft tissue applications and is within the scope of this disclosure.

Figure 28:
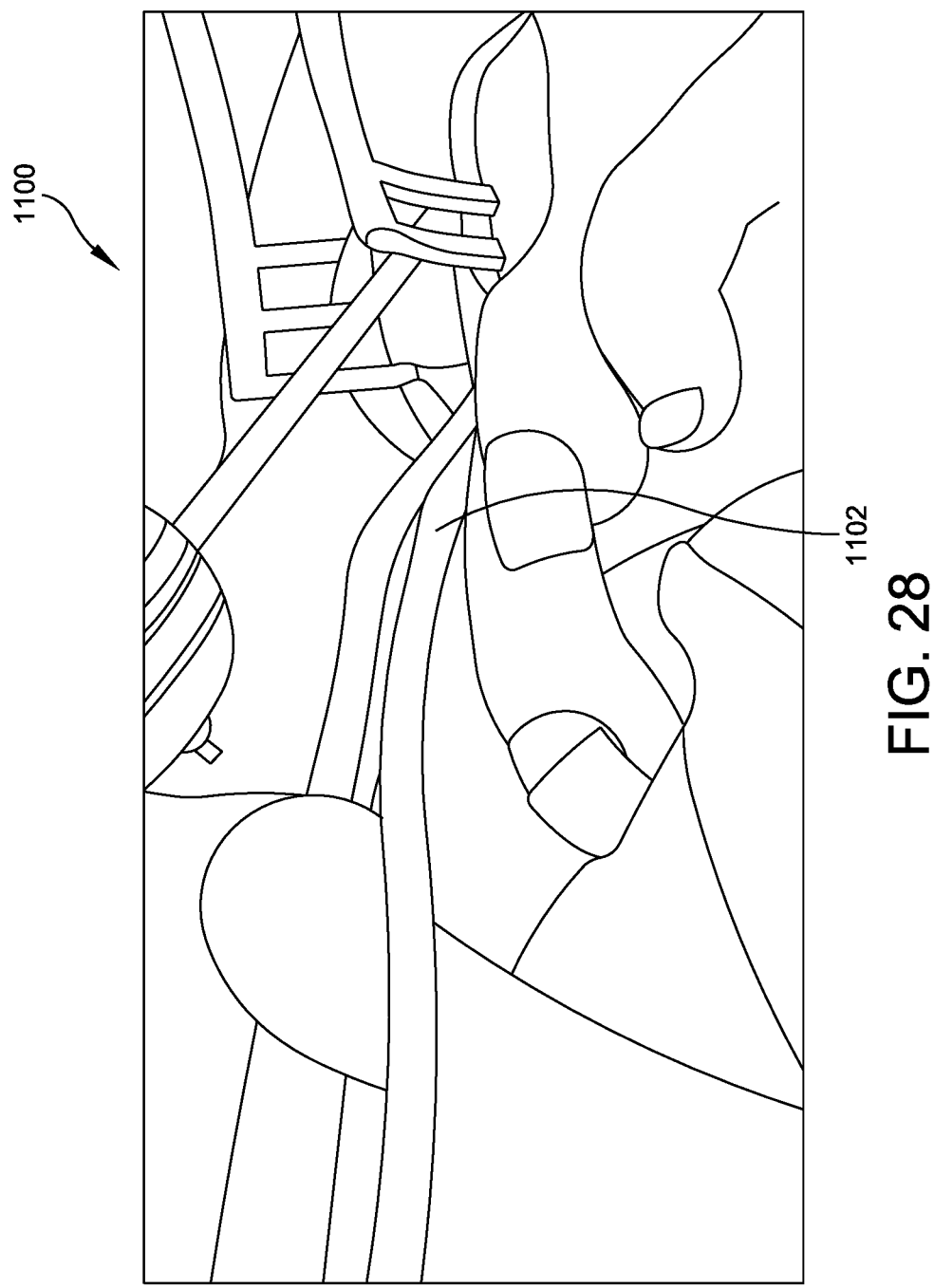
FIG. 28 illustrates a soft tissue release of a joint, in accordance with some embodiments.

At step 1004, soft tissue and/or connective tissue is released from a portion of the exposed joint. For example, as illustrated in FIG. 28, one or more dorsal capsular and/or collateral ligaments can be released from a proximal phalanx of an MTP joint 1100. An elevator 1102 is used to release a soft tissue section, such as a plantar plate, from a distal metatarsal of an MTP joint. In other embodiments, alternative and/or additional connective tissue (e.g., ligaments, tendons, etc.) and/or soft tissue can be released from any portion of an exposed joint.

Figure 29:
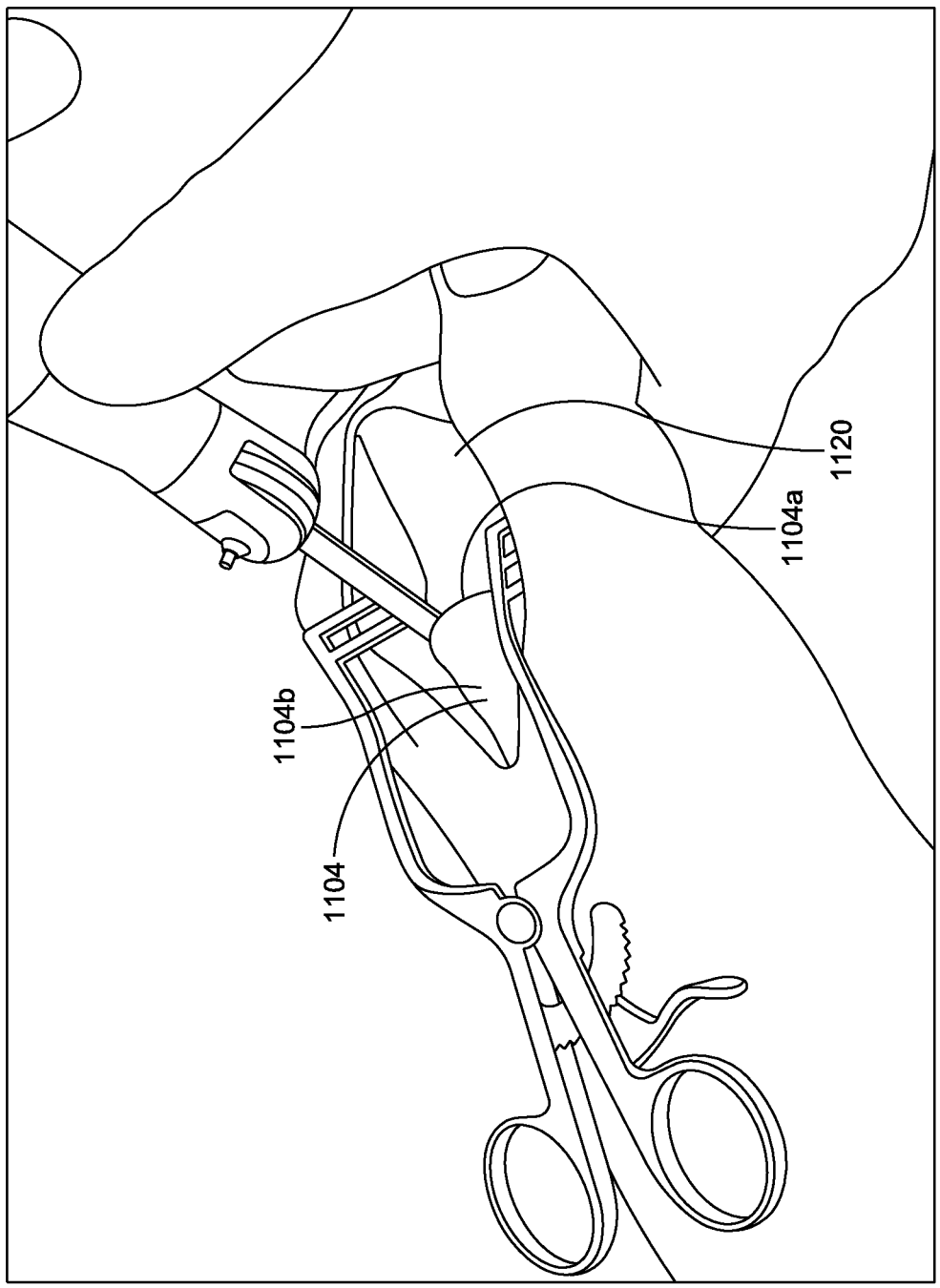
FIG. 29 illustrates formation of an osteotomy in a first bone, in accordance with some embodiments.
Figure 30:
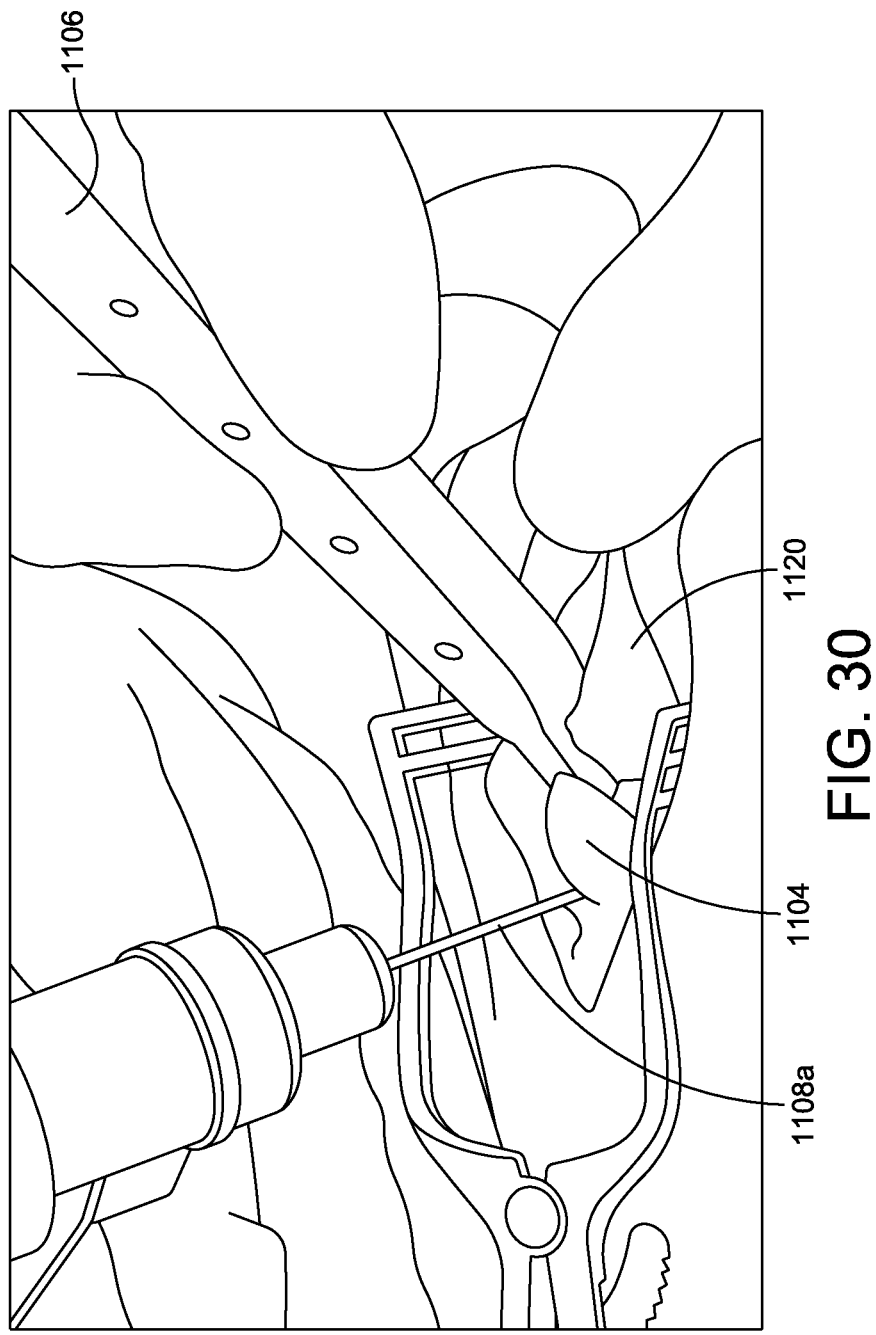
FIG. 30 illustrates separation and temporary fixation of a first bone fragment from a second bone fragment, in accordance with some embodiments.

At step 1006, an osteotomy is formed in a first bone 1104 of the joint 1100. For example, as shown in FIG. 29, an osteotomy can be formed in a distal metatarsal. The osteotomy can provide for shortening of a first bone 1104 of the joint. In some embodiments, the osteotomy separates the first bone 1104 into a first bone fragment 1104a and a second bone fragment 1104b.

At step 1008, the first bone fragment 1104*a* is displaced proximally from the second bone fragment 1104*b*. In some embodiments, the first bone fragment 1104*a* is a capital fragment of a metatarsal formed as a result of the osteotomy of step 1006. In the illustrated embodiment, the first bone fragment 1104*a* and the second bone fragment 1104*b* are temporarily fixed using a k-wire 1108*a*, although it will be appreciated that any suitable temporary fixation device, such as a k-wire, a screw, a pin, etc. can be used to temporarily fixate the first bone fragment 1104*a* and the second bone fragment 1104*b*.

Figure 31:
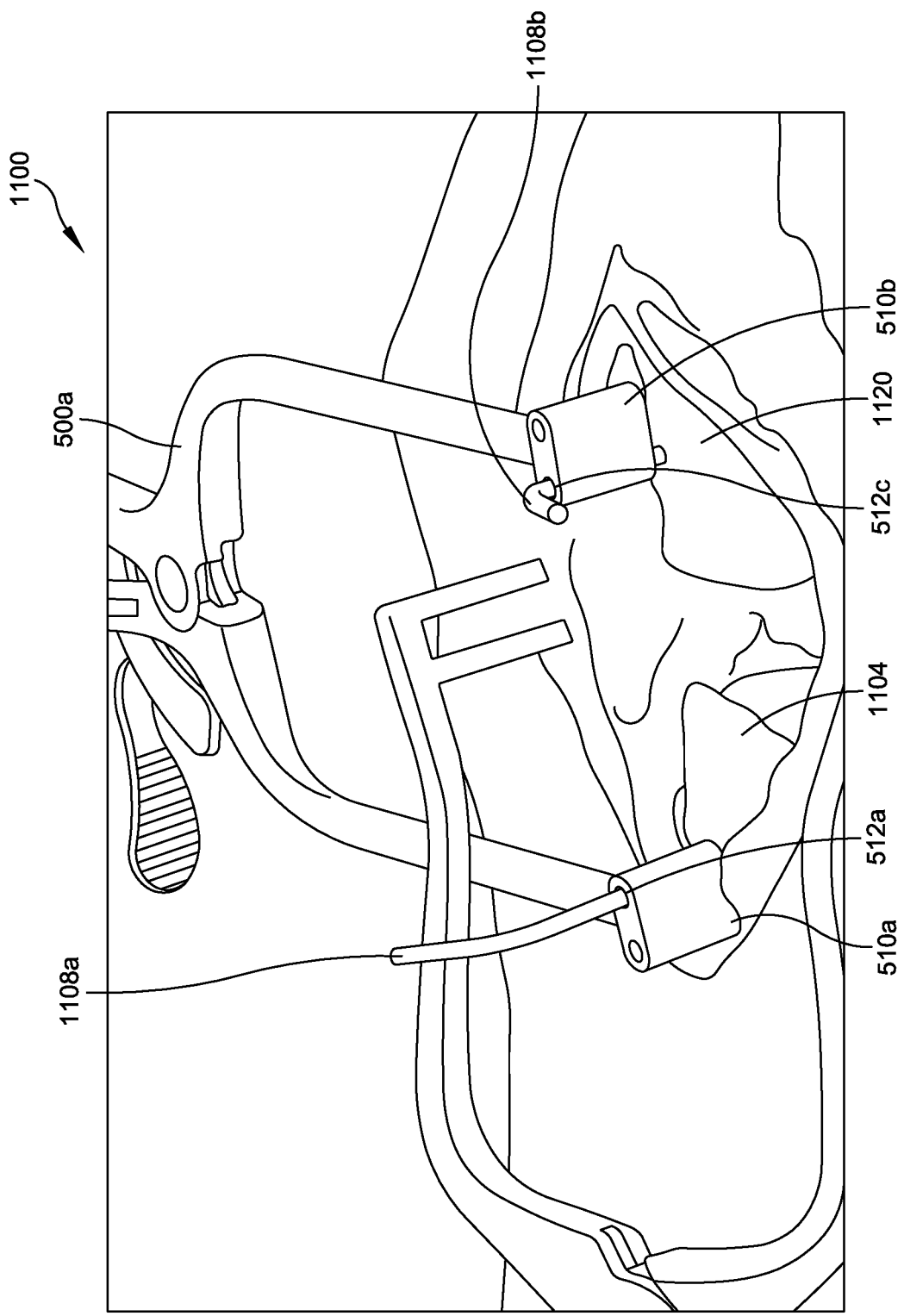
FIG. 31 illustrates distraction of a first bone from a second bone, in accordance with some embodiments.

At step 1010, a distractor 500 is coupled to the first bone 1104 and the second bone 1120. As shown in FIG. 31, in some embodiments, a first hole 512*a* formed in a first anchoring body 510*a* of the distractor 500 is coupled to the first k-wire 1108*a* and a second k-wire 1108*b* coupled to the second bone 1120. The second k-wire 1108*b* is inserted through a hole 512*c* defined in the second anchoring body 510*b* after coupling the first anchoring body 510*a* to the first k-wire 1108*a*, although it will be appreciated that the second k-wire 1108*b* can be coupled to the second bone 1120 prior to coupling the first anchoring body 510*a* to the first k-wire 1108*a*.

At step 1012, the first bone 1104 is distracted from the second bone 1120. The first and second bones 1104, 1120 can be distracted by actuating the handles 506*a*, 506*b* of the distractor 500 to separate the first anchoring body 510*a* from the second anchoring body 510*b*. The first bone fragment 1104*a* and the second bone fragment 1104*b* of the first bone 1104 are moved together by the distractor 500, as the first bone fragment 1104*a* and the second bone fragment 1104*b* are coupled by the k-wire 1108*a*. As shown in FIG. 31, the first bone 1104 and the second bone 1120 are distracted to provide access to a soft tissue section and allow insertion of one or more surgical instruments to the soft tissue section, as discussed in greater detail below.

At optional step 1014, additional fixation elements are inserted through the anchoring bodies 510*a*, 510*b* of the distractor 500 and/or the bones 1104, 1120 to provide secondary fixation of the bones 1104, 1120. The additional fixation elements can include any suitable fixation element, such as a k-wire, a screw, a pin, and/or any other suitable fixation element. In other embodiments, the additional fixation elements are omitted and the distractor 500 is coupled to the bones 1104, 1120 by the primary fixation elements 1108*a*, 1108*b* only.

Figure 32:
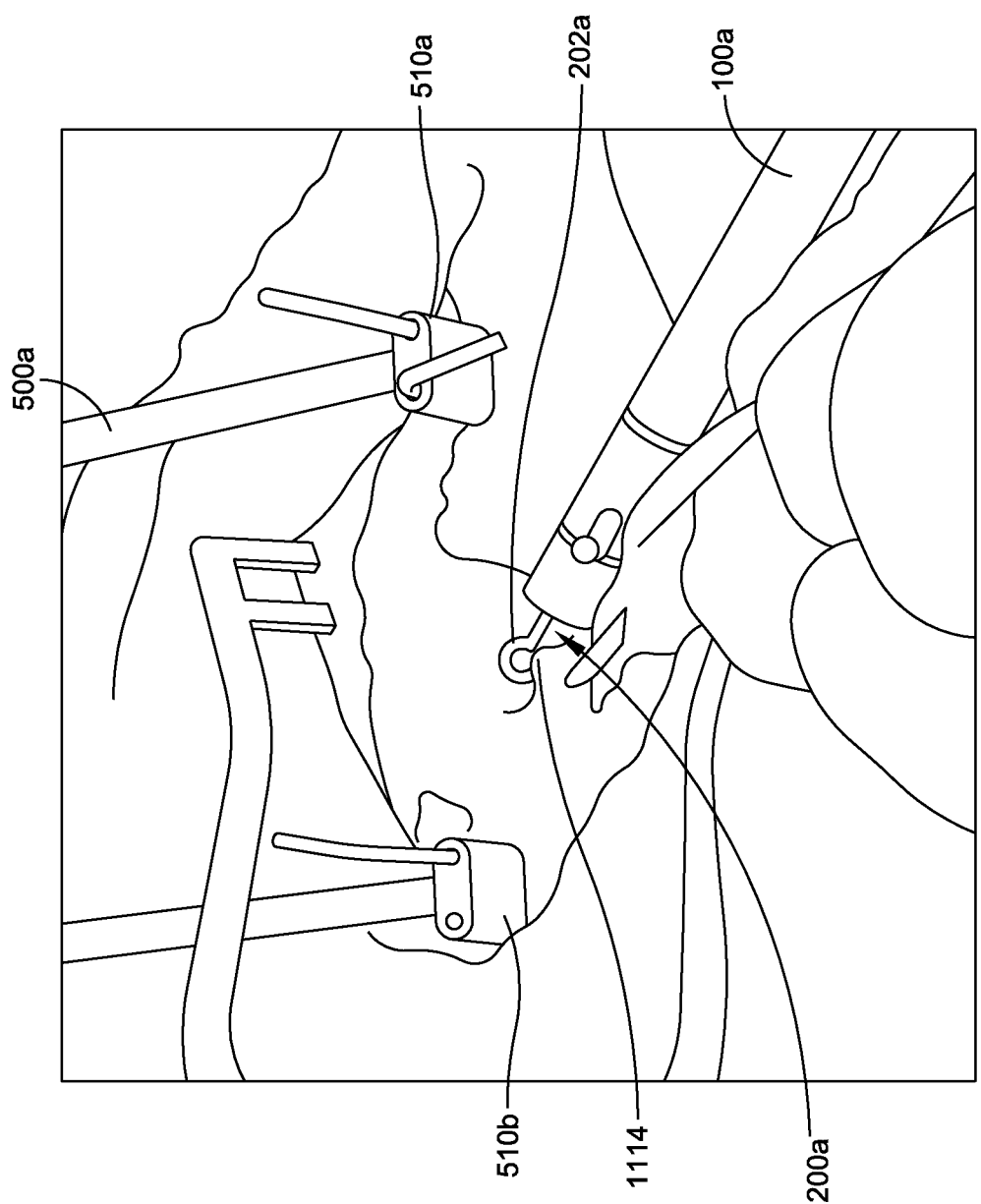
FIG. 32 illustrates insertion of a flexible strand into a soft tissue section, in accordance with some embodiments.
Figure 33:
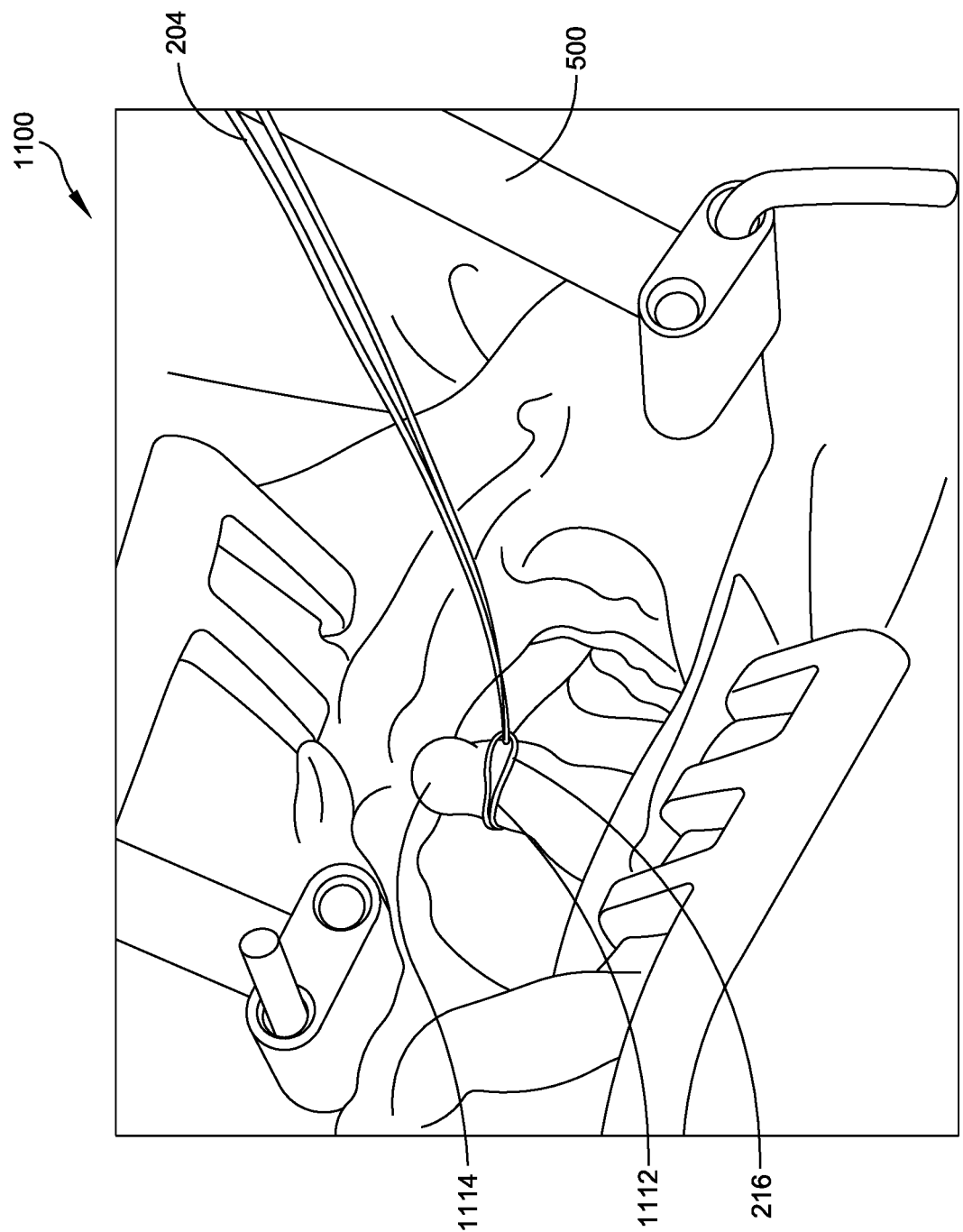
FIG. 33 illustrates the flexible strand of FIG. 32 coupled to the soft tissue section, in accordance with some embodiments.
Figure 34:
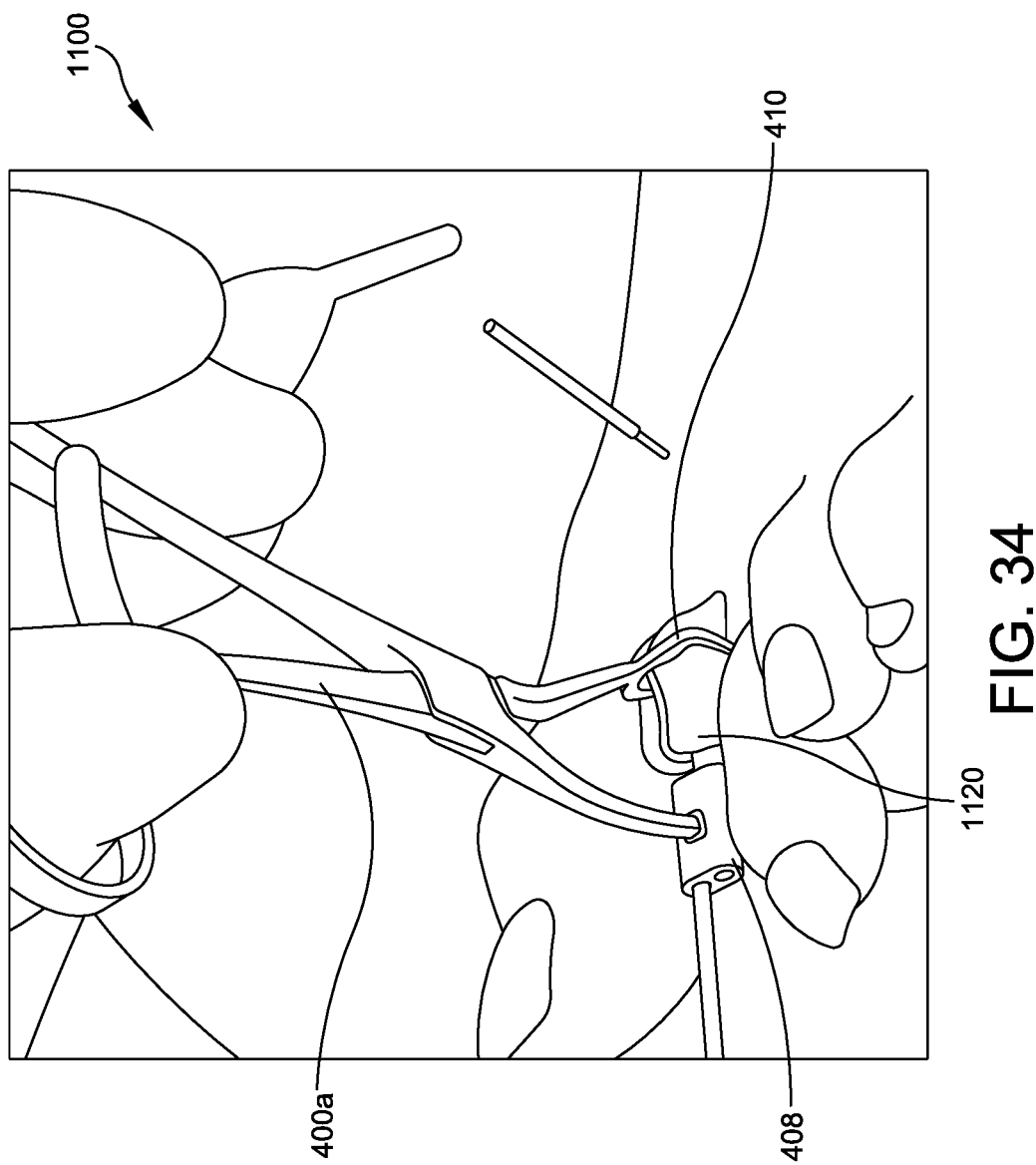
FIG. 34 illustrates a clamping drill guide coupled to a second bone, in accordance with some embodiments.
Figure 35:
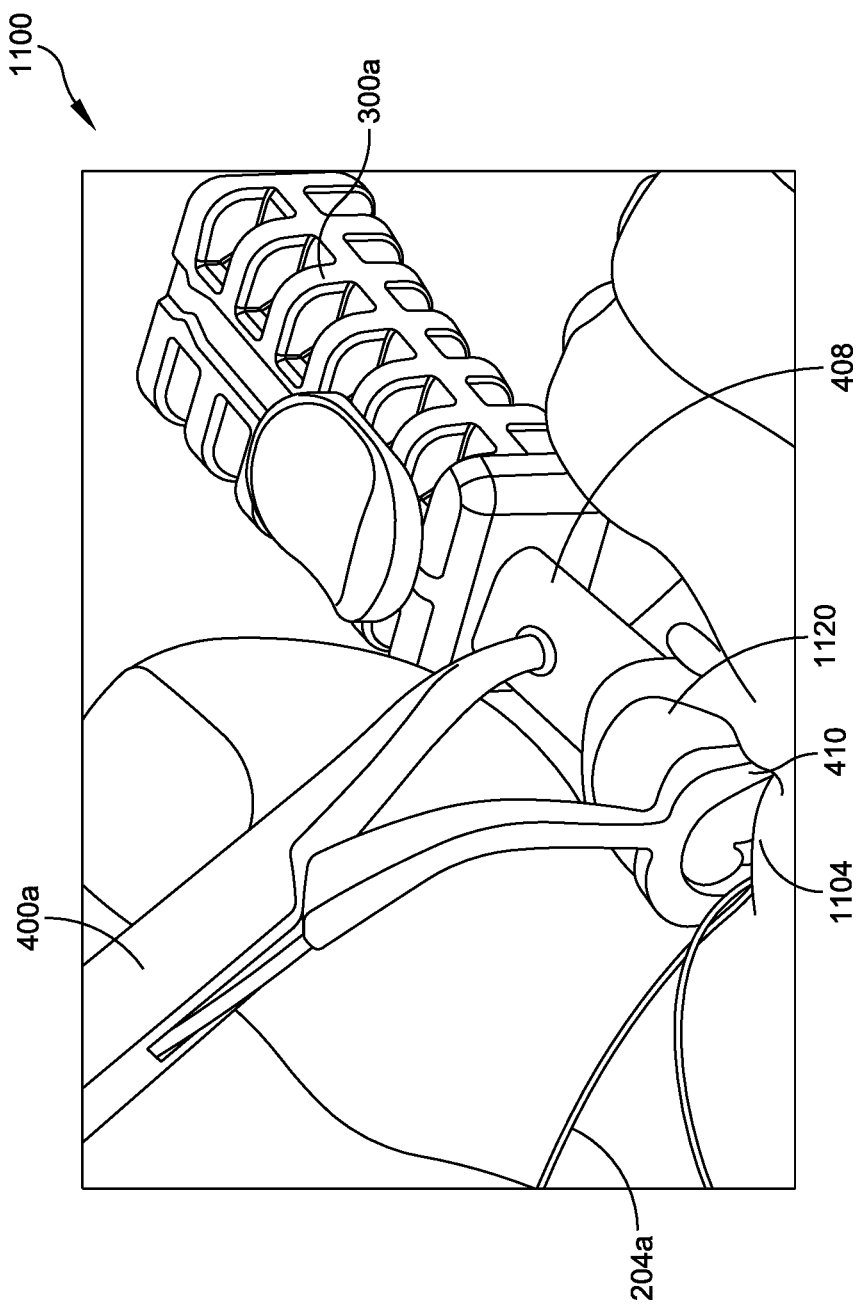
FIG. 35 illustrates insertion of a strand retriever through a clamping drill guide coupled to a second bone section, in accordance with some embodiments.

At step 1016, a needle construct is coupled to the soft tissue section 1114. As illustrated in FIG. 32, a first needle construct 200*a* is coupled to and implanted by a first driver 100*b* configured to apply an insertion force to a first needle 202*a* of the first needle construct 200*a*. The first driver 100*b* is similar to the driver 100 discussed above, and similar description is not repeated herein. The first driver 100*b* transfers an insertion force, such as a torsional insertion force, from the body 102 to the first needle 202*a*, which penetrates the soft tissue section 1114. After insertion of the first needle 202 at least partially into the soft tissue section 1114, the first needle construct 200*a* is released from the first driver 100*b*, for example, by depressing a button 140 to release a locking element 126 of the driver 100*b*.

At optional step 1018, the first needle construct 200*a* can be retracted into the first driver 100*b* and redeployed in the same and/or an alternative location. A method of retracting and redeploying the first needle construct 200*a* is discussed in greater detail below with respect to FIGS. 40-45.

At step 1020, the first flexible strand 204*a* of the first needle construct 200*a* is coupled to the soft tissue section 1114. In the embodiment shown in FIG. 33, the first flexible strand 204*a* defines a loop 216 and is coupled to the soft tissue section 1114 by passing the needle 202*a* and the attached flexible strand 204 through the loop 216 to form a knot 1112 around the tissue 1114. The knot 1112 can be any suitable knot, such as, for example, a slip-knot (luggage-tag style knot, hitch knot, etc.), a fixed knot, and/or any other suitable knot. Although embodiments are discussed herein including a luggage tag-style knot, it will be appreciated that any suitable knot, anchor, and/or any other suitable element can be used to anchor the first flexible strand 204*a* to the soft tissue section 1114.

In some embodiments, steps 1016-1020 can be repeated to couple one or more additional needle constructs to the soft tissue section 1114. For example, in some embodiments, a second needle construct (not shown) including a second needle 202*b* and a second flexible strand 204*b* are coupled to the soft tissue section 1114 at a second position. Although embodiments are discussed herein including two needle constructs, it will be appreciated that any suitable number of needle constructs 200*b* can be coupled to the soft tissue section 1114.

At step 1022, the distractor 500 and/or the temporary fixation elements 1108*a*, 1108*b* can be removed from the first bone 1104 and/or the second bone 1120. For example, in some embodiments, the distractor 500 is removed from the temporary fixation elements 1108*a*, 1108*b* by sliding the anchor bodies 508*a*, 508*b* dorsally over the fixation elements 1108*a*, 1108*b*. The fixation elements 1108*a*, 1108*b* can be subsequently removed from the bones 1104, 1120.

At step 1024, a clamping drill guide 400 is coupled to a second bone 1120, such as a proximal phalanx. As discussed above, the clamping drill guide 400 includes a guide element 408 and a clamping element 410 coupled in pivoting arrangement. The second bone 1120 is positioned between the guide element 408 and the clamping element 410 and a force is applied to the handle portion 402 to clamp the second bone 1120 between the guide element 408 and the clamping element 410. In some embodiments, the clamping drill guide 400 includes a locking element 424 configured to maintain the guide element 408 and the clamping element 410 in a clamped position during surgery.

At step 1026, the trajectory of the guide holes 414*a*, 414*b* formed in the guide element 408 is confirmed. The trajectory of the guide holes 414*a*, 414*b* can be confirmed by coupling a trajectory guide 450 to the clamping drill guide 400. The trajectory guide 450 includes a post 452 configured to indicate a path of the guide holes 414*a*, 414*b* when the trajectory guide 450 is coupled to the clamping drill guide 400. For example, in some embodiments, when viewed sagittally, the post 452 indicates a path of the drill guide holes 414*a*, 414*b*. The trajectory guide 450 is used to ensure that a hole forming element inserted through the drill guide holes 414*a*, 414*b* will not violate the articular surface of the bone. The clamping drill guide 400 can be adjusted as required to properly align the guide holes 414*a*, 414*b*.

At step 1028, at least one hole is formed through the second bone 1120. In some embodiments, the at least one hole is formed by inserting a bit element, such a k-wire or a drill bit, through a guide hole 414*a*, 414*b* of the clamping drill guide 400. The bit element penetrates the second bone 1120 and extends through the opening 418 defined by the clamping element 410 of the clamping drill guide 400.

At step 1030, a first longitudinal tube 314*a* and a second longitudinal tube 314*b* of a strand retriever 300 are inserted into respective first and second guide holes 414*a*, 414*b* of the clamping drill guide 400 on a dorsal (or first) side of the second bone 1120. In some embodiments, a portion of the longitudinal tubes 314a, 314b extends plantarly beyond the guide element 408 of the clamping drill guide and into one or more tunnels formed in the second bone 1120, although it will be appreciated that the longitudinal tubes 314a, 314b can extend partially through the guide element 408.

Figure 36:
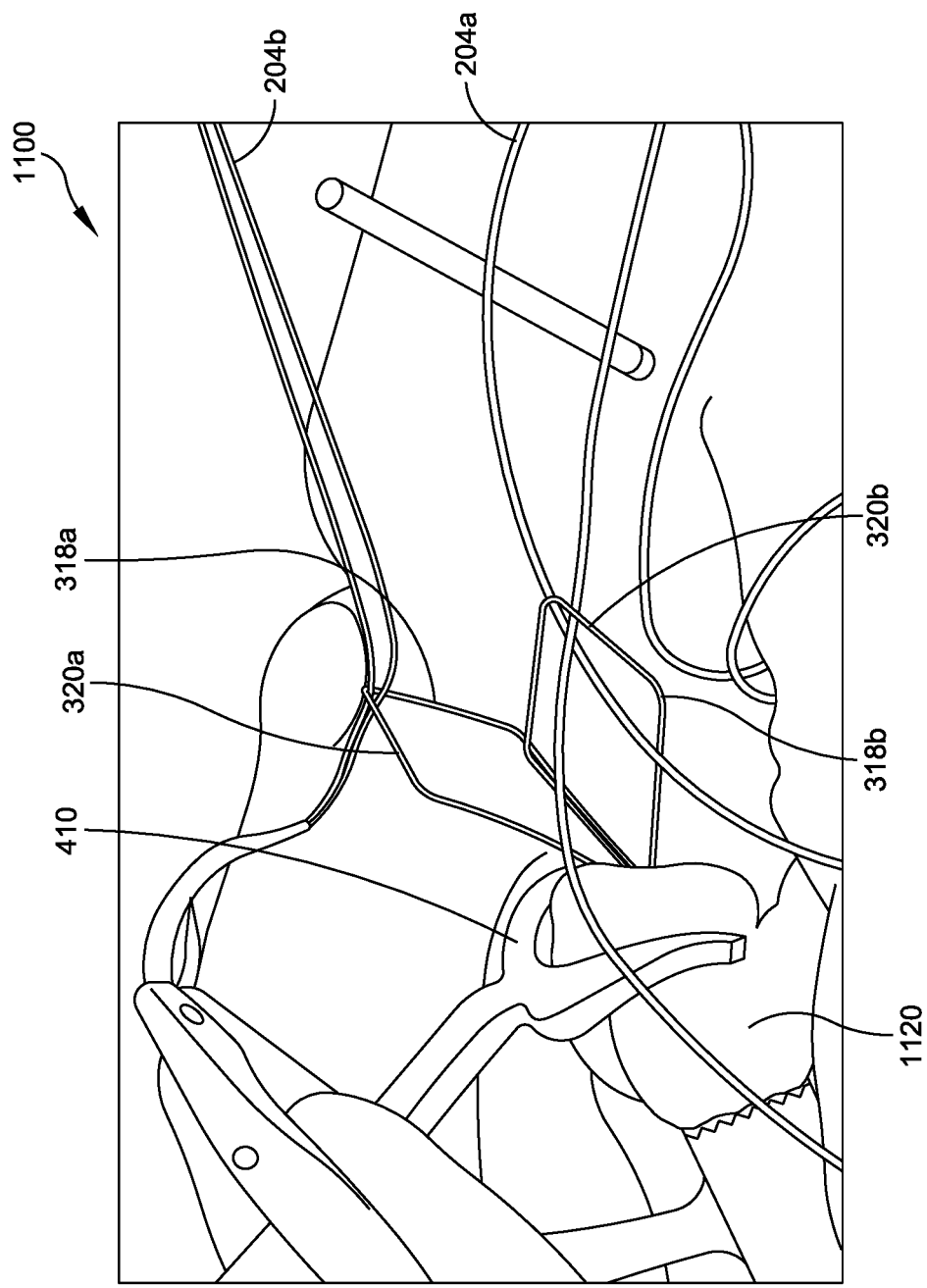
FIG. 36 illustrates the first and second snares of the strand retriever deployed to a plantar side of the second bone section through the clamping drill guide, in accordance with some embodiments.

At step 1032, a first snare 318a and a second snare 318b are deployed from the longitudinal tubes 314a, 314b to a plantar (or second) side of the second bone 1120. As shown in FIG. 36, the snares 318a, 318b extend plantarly beyond the second bone 1120. After being deployed, the snares 318a, 318b expand to define loops 320a, 320b sized and configured to receive a respective needle 202a, 202b and/or a respective flexible strand 204a, 204b therethrough.

At step 1034, a flexible strand 204a of a first needle construct 200a is passed through the loop 320a of the first snare 318a. In some embodiments, the needle 202a of the first needle construct 202a is advanced through the loop 320a of the first snare 318a to pass the flexible strand 204a therethrough. The flexible strand 204a can be passed through the loop 320a of the first snare 318a once and/or multiple times. As shown in FIG. 36, in some embodiments, a flexible strand 204b of a second needle construct 200b is passed through the loop 320b of a respective second snare 318b. The needles 202a, 202b can be removed from the respective flexible strands 204a, 204b prior to and/or after passing the flexible strands 204a, 204b through a respective loop 320a, 320b. The needles 202a, 202b can be removed by cutting or otherwise disconnecting the needles 202a, 202b from the respective flexible strands 204a, 204b.

Figure 37:
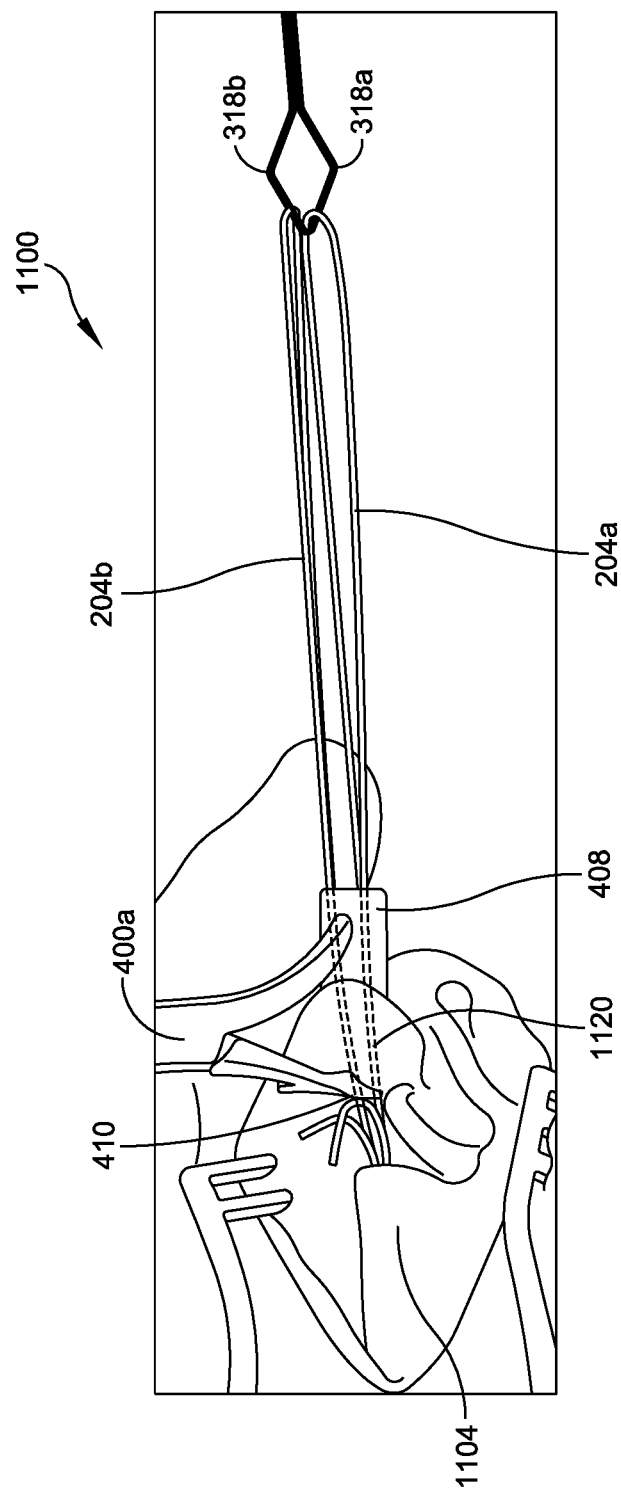
FIG. 37 illustrates first and second flexible strands extending from a plantar side of the second bone to a dorsal side of the second bone after retrieval through the clamping drill guide, in accordance with some embodiments.

At step 1036, the flexible strands 204a, 204b are pulled through the bone tunnels formed in the second bone 1120 to a dorsal side of the second bone 1120 and tensioned. The flexible strands 204a, 204b can be retrieved by withdrawing the strand retriever 300 dorsally, which causes the loops 320a, 320b of each of the snares 318a, 318b to be pulled through the second bone 1120 and the guide element 408 of the clamping drill guide. The snares 318a, 318b pull the flexible strands 204a, 204b through the second bone 1120 and the clamping drill guide 400 as they are withdrawn dorsally. In some embodiments, the entire strand retriever 300 is withdrawn dorsally from the second bone 1120. In other embodiments, the snares 318a, 318b are withdrawn dorsally by actuating the slider 330 prior to withdrawing the strand retriever 300 from the second bone 1120. FIG. 37 illustrates the first and second flexible strands 204a, 204b in a dorsal position after retrieval through the clamping drill guide 400. In some embodiments, knot 1114 is a self-tightening knot that is tensioned and/or tightened prior to, during, and/or after retrieval of the flexible strands 204a, 204b through the second bone 1120.

At step 1038, the bone fragments 1104a, 1104b are fixed in a desired position. A fixation device is inserted into one or more fragments 1104a, 1104b to anchor the fragments 1104a, 1104b in a desired position. For example, in some embodiments, a snap-off screw is inserted into the fragments 1104a, 1104b, although it will be appreciated that any fixation device can be used to fix the position of the fragments 1104a, 1104b.

Figure 38:
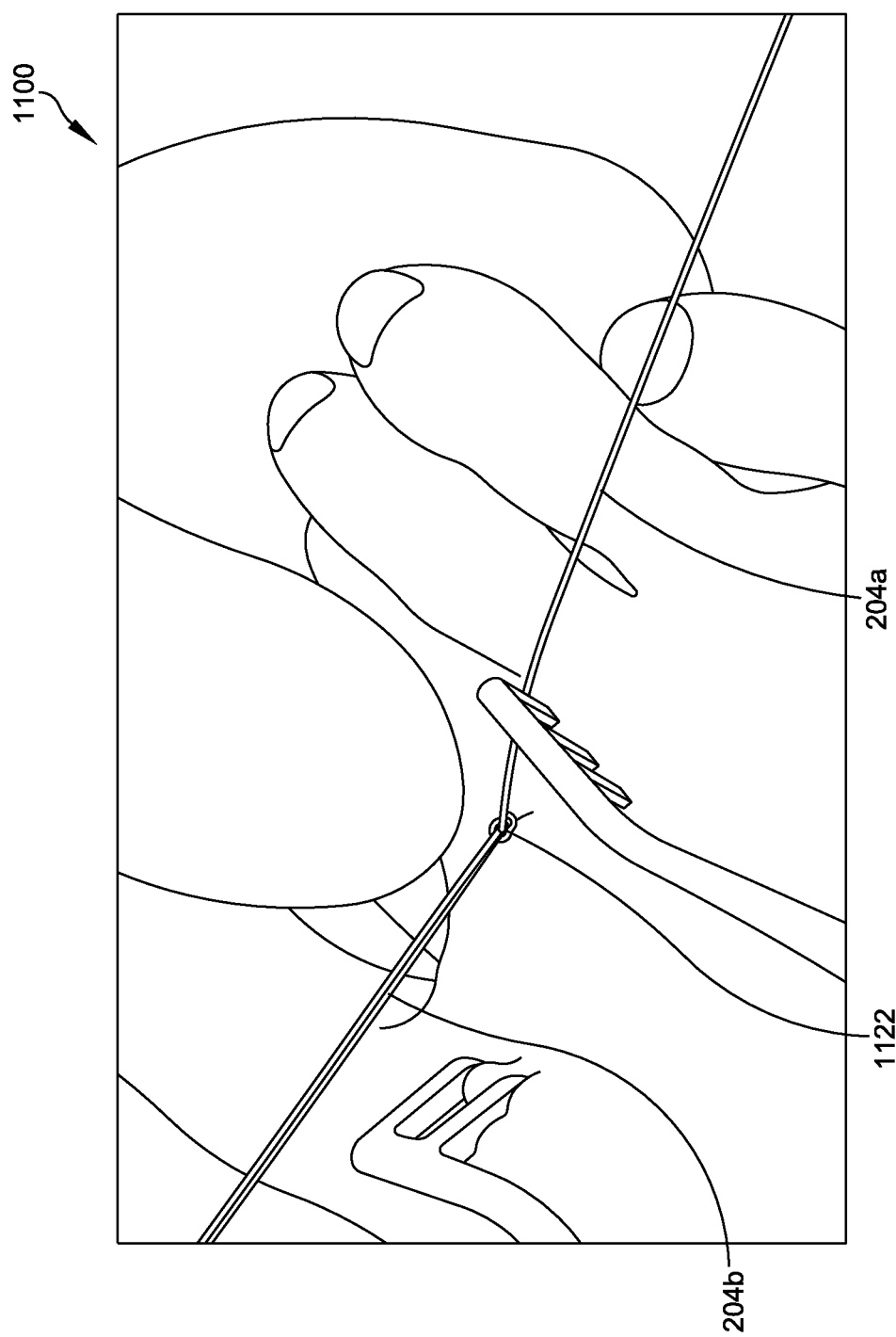
FIG. 38 illustrates tensioning of the first and second flexible strands to position the soft tissue section, in accordance with some embodiments.
Figure 39:
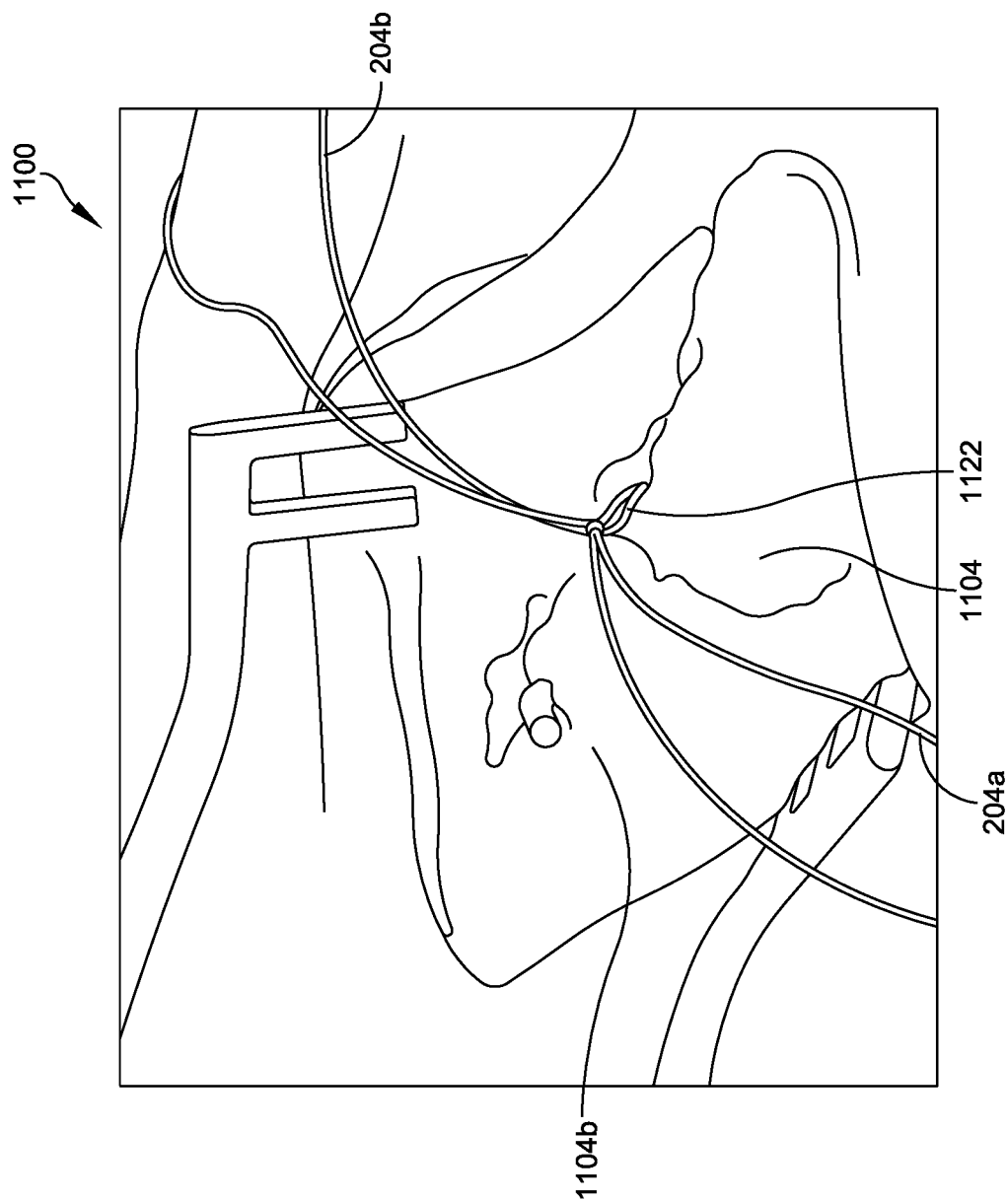
FIG. 39 illustrates a knot formed in the first and second flexible strands to couple the soft tissue section to the second bone, in accordance with some embodiments.

At step 1040, the soft tissue section 1114 is positioned by applying tension to the flexible strands 204a, 204b extending from the second bone 1120 to draw the soft tissue section 1114 into contact with the second bone fragment 1104b. In some embodiments, knot 1114 is a self-tightening knot that is tensioned and/or tightened prior to, during, and/or after positioning of the soft tissue section 1114. As shown in FIGS. 38 and 39, a knot 1122 can be formed in one or more of the flexible strands 204a, 204b to anchor the soft tissue section 1114 in a predetermined position with respect to the first bone 1104 and/or the second bone 1120. In other embodiments, a knotless anchor system can be used to secure one or more of the flexible strands 204a, 204b.

Figure 40:
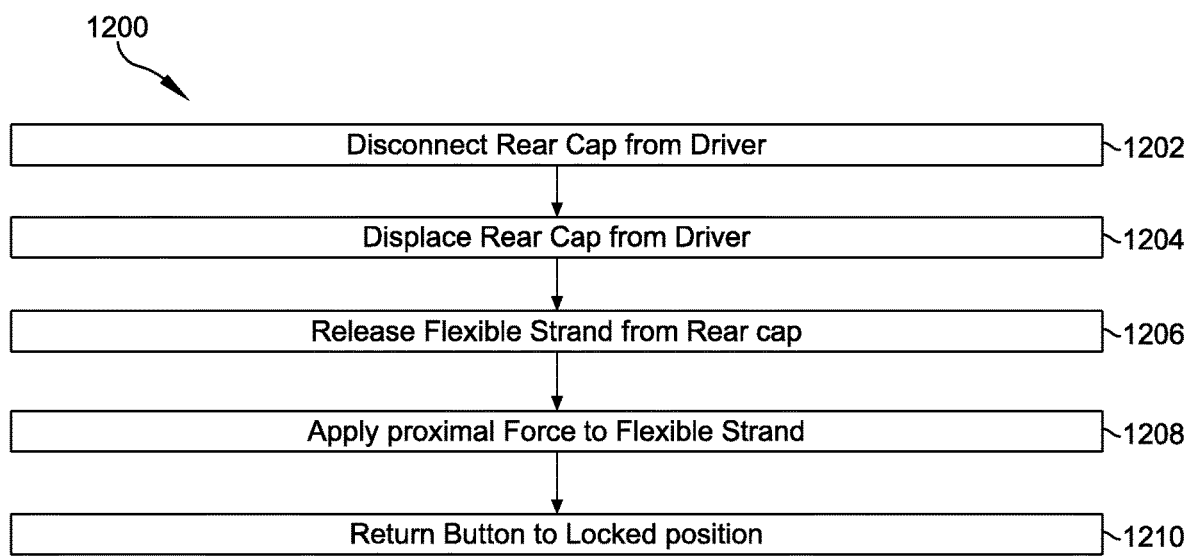
FIG. 40 illustrates a method of retracting a needle and flexible strand after deployment from a driver, in accordance with some embodiments.
Figure 41:
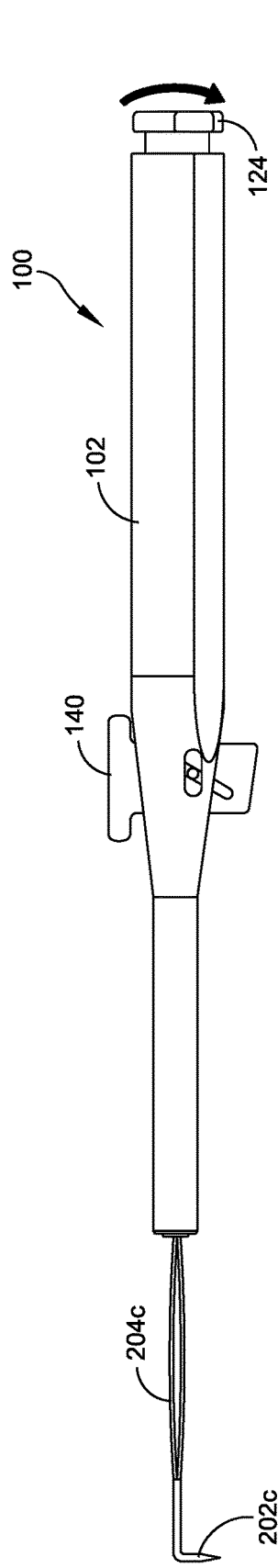
FIG. 41 illustrates a driver coupled to a needle construct having a needle and a flexible strand in a deployed position, in accordance with some embodiments.

FIG. 40 is a flowchart illustrating a method 1200 of retrieving and redeploying a needle construct 200c from a driver 100c and FIGS. 41-44 illustrate various steps of the method 1200, in accordance with some embodiments. As shown in FIG. 41, at the start of method 1200, the needle construct 200c is in a deployed position with the needle 202c released from and positioned distally of the opening 120. The flexible strand 204c extends from the needle 202c and into the body 102 of the driver 100. At step 1202, a cap 124 is removed from the body 102 of the driver 100. The cap 124 can be removed by applying a rotational and/or longitudinal force to the rear cap 124 to separate the cap 124 from the body 102.

Figure 42:
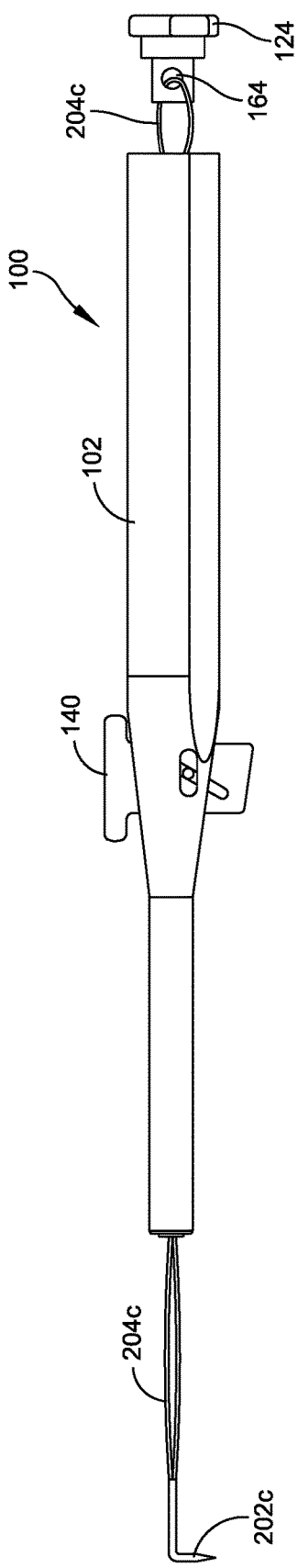
FIG. 42 illustrates the driver of FIG. 41 having a cap removed from a proximal end of the driver, in accordance with some embodiments.
Figure 43:
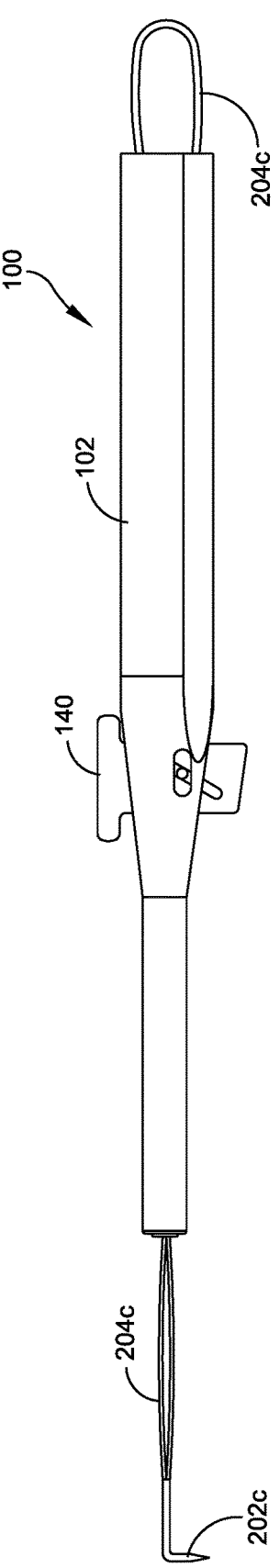
FIG. 43 illustrates the driver of FIG. 42 having the flexible strand decoupled from the cap, in accordance with some embodiments.
Figure 44:
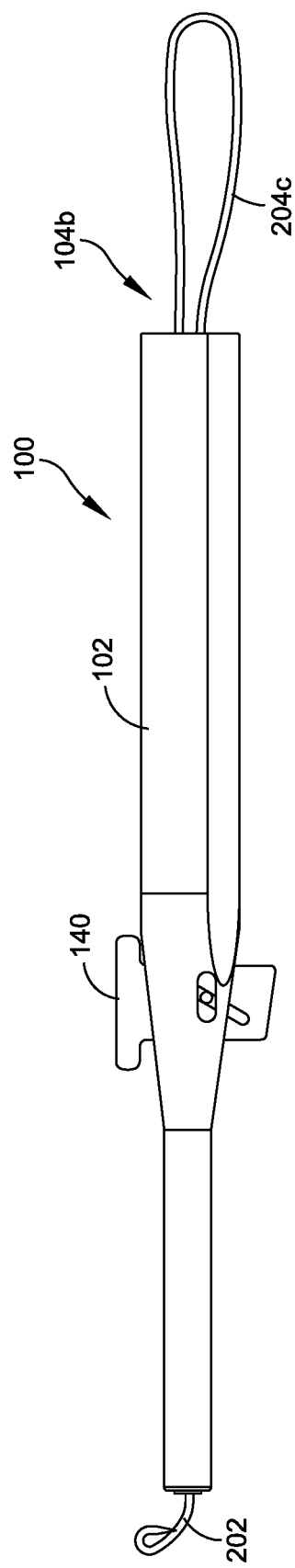
FIG. 44 illustrates the driver of FIG. 43 after retraction of the needle and flexible strand of the needle construct, in accordance with some embodiments.
Figure 45:
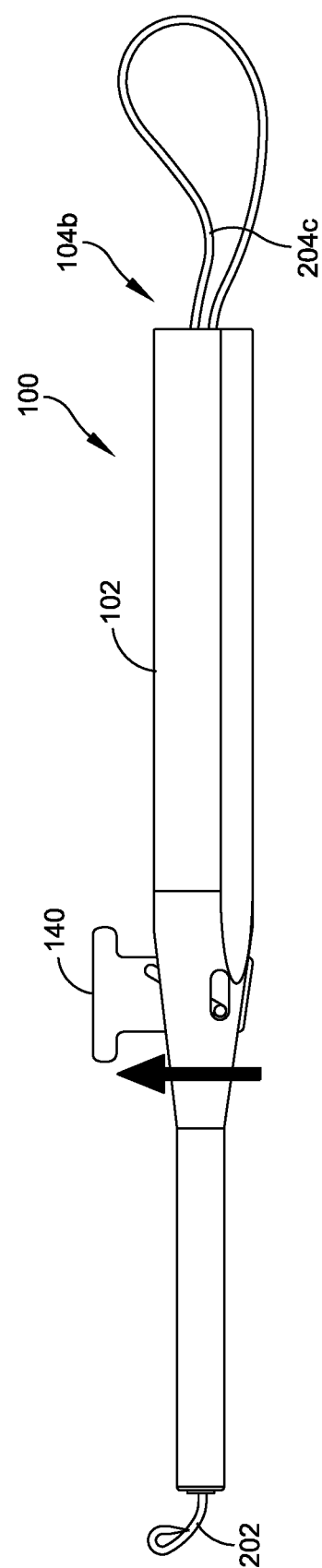
FIG. 45 illustrates the driver of FIG. 44 having a needle construct coupled thereto in a fixed relationship, in accordance with some embodiments.

At step 1204, the cap 124 is displaced proximally from body 102, as shown in FIG. 42. The cap 124 includes a boss 166 coupled to the flexible strand 204c. For example, in some embodiments, the boss 166 defines a hole 168 and the flexible strand 204c is looped at least once through the hole 168, although it will be appreciated that the flexible strand 204c can be coupled to the cap 124 using any suitable coupling mechanism.

At step 1206, the flexible strand 204 is disconnected from the cap 124. After disconnecting the cap 124, a proximal end 208 of the flexible strand 204c extends from a proximal end 104b of the body 102.

At step 1208, a proximal force is applied to the flexible strand 204c to draw the flexible strand 204c and the needle 202c proximally. The flexible strand 204c is withdrawn proximally until the non-circular mating portion 214 of the needle 202c is positioned within the opening 120 of the driver 100c. In some embodiments, the needle 202c is rotated while applying the proximal force to the flexible strand 204c to ensure a proper engagement between the non-circular mating portion 214 of the needle 202c and the non-circular needle opening 120 of the driver 100c.

At step 1210, the button 140 is returned to a locked position to lock the flexible strand 204c and the needle 202c in a fixed position with respect to the driver 100c. As discussed above, a locking element 126 maintains the flexible strand 204c and/or the needle 202c in a fixed position when the button 140 is in a locked position. Because the flexible strand 204c and/or the needle 202c are maintained by the locking element 126, the driver 100c can be used without recoupling the cap 124 to the distal end 104a of the body 102, although in some embodiments the cap 124 can be recoupled to the body 102 prior to reinsertion of the needle 202c in a tissue section. The driver 100c can be used to implant the needle 202c according to one or more steps of the method 1000 discussed above.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

What is claimed is:

1. A method, comprising: passing a first flexible strand through a tissue section, wherein the first flexible strand is passed through the tissue section by a first needle coupled to a driver, the driver comprising a longitudinal body defining an opening at a distal end, wherein the first needle is positioned in the opening;
   forming a first hole through a bone adjacent to the first tissue section; passing the first suture through the first hole using a strand retriever, wherein the strand retriever comprises a body having a first longitudinal tube extending therefrom and a first snare deployable from the first longitudinal tube, wherein the first longitudinal tube is positioned from a first side of the bone within the first hole formed in the first bone and the first snare is deployed on a second side of the bone, and wherein the first snare passes the first flexible strand through the first hole in the bone; and securing the tissue section to the bone using the first flexible strand; and wherein insertion of the needle comprises transferring a torsional force from the driver to the needle; and wherein the needle opening of the longitudinal driver defines a non-circular cross-section and the needle defines a non-circular mating portion, and wherein the torsional force is transferred from the non-circular cross-section to the non-circular mating portion.

2. The method of claim 1, wherein the first flexible strand extends into a cavity defined in the longitudinal body and is maintained in a fixed position with respect to the longitudinal body by a locking element.

3. The method of claim 1, comprising releasing the first flexible strand from the longitudinal body by transitioning a locking element from a locked position to an unlocked position.

4. The method of claim 3, wherein the locking element is configured to apply a frictional locking force to the flexible strand in a locked position.

5. The method of claim 1, comprising passing a second flexible strand through the tissue section, wherein the second flexible strand is passed through the tissue section by a second needle coupled to a second driver;

forming a second hole through the bone;

passing the second flexible strand through the second hole using the strand retriever, wherein the strand retriever comprises a second longitudinal tube extending therefrom and a second snare slideably deployable from the second longitudinal tube, wherein the second longitudinal tube is positioned from the first side of the bone within the second hole formed in the bone and the second snare is deployed on the second side of the bone, and wherein the second snare passes the second flexible strand through the second hole in the bone.

6. The method of claim 1, wherein forming the first hole through the first bone comprises:

clamping the bone in a clamping drill guide comprising a guide element and a clamping element in a hinged engagement; and inserting a hole forming element through a first guide hole formed in the guide element, wherein the hole forming element is configured to form the first hole through the bone.

7. The method of claim 6, wherein passing the first flexible strand through the first hole comprises inserting the first longitudinal tube through the first guide hole.

8. The method of claim 1, comprising coupling the first flexible strand to the tissue section by forming a knot in the first flexible strand after passing the first needle through the tissue section.

9. The method of claim 8, wherein the knot is a luggage-tag knot.

* * * * *